US007407675B2

(12) United States Patent
Einbond et al.

(10) Patent No.: US 7,407,675 B2
(45) Date of Patent: Aug. 5, 2008

(54) ANTI-NEOPLASTIC COMPOSITIONS COMPRISING EXTRACTS OF BLACK COHOSH

(75) Inventors: Linda Saxe Einbond, Crestwood, NY (US); I. Bernard Weinstein, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/746,960

(22) Filed: Dec. 23, 2003

(65) Prior Publication Data

US 2005/0008717 A1 Jan. 13, 2005

Related U.S. Application Data

(60) Provisional application No. 60/437,159, filed on Dec. 27, 2002.

(51) Int. Cl.
*A61K 36/28* (2006.01)
(52) U.S. Cl. .................................. 424/764
(58) Field of Classification Search .............. 424/764; 514/2, 783
See application file for complete search history.

(56) References Cited

U.S. PATENT DOCUMENTS 5,972,986 A * 10/1999 Seibert et al.

FOREIGN PATENT DOCUMENTS

JP 09030977 A * 2/1997

OTHER PUBLICATIONS

Bedir, E. et al., Chem. Pharm. Bull. (2000), 48(3): 425-427. Cimiracemoside A: A new cycloanostanol xyloside from the rhizome of *Cimicifuga racemosa*.*
Corsano, S. Corsi e Seminari di Chimica, Consiglio Nazionale delle Ricerche e Fondazione F. Giordani (1968), 11, 61-4. Structure of the glucoside acetin.*
http://www.holistic-online.com/Herbal-Med/_Herbs/h32.htm.*
Gura, T. Science, 1997, 278:1041-1042. Systems for identifying new drugs are often faulty.*
Jain, R. K. Sci. Am., 1994, 271:58-65. Barriers to drug delivery in solid tumors.*
Curti, B. D. Crit. Rev. in Oncology/Hematology, 1993, 14:29-39. Physical barriers to drug delivery in tumors.*
Beers and Berkow, eds., The Merck Manual of Diagnosis and Therapy, 17th ed. (Whitehouse Station, N. J.: Merck Research Laboratories, 1999). 973-974, 976, 986, 988, 991.
Bodinet and Freudenstein, Influence of *Cimicifuga racemosa* on the proliferation of estrogen receptor-positive human breast cancer cells. Breast Cancer Research and Trearment, 76:1-10, 2002.
Burdette, et al., Black cohosh (*Cimicifuga racemosa* L.) protects against menadione-induced DNA damage through scavenging of reactive oxygen species: bioassay-directed isolation and characterization of active principles. J. Agric. Food Chem., 50: 7022-7028, 2002.
Chen et al., Isolation, structure elucidation, and absolute configuration of 26-deoxyactein from *Cimicifuga racemosa* and clarification of nomenclature associated with 27-deoxyactein. J. Nat. Prod., 65: 601-605, 2002.
Chou and Talalay, Quantitative analysis of dose-effect relationships: the combined effects of multiple drugs or enzyme inhibitors. Adv. Enzyme Regul., 22: 27-55, 1984.
Dixon-Shanies and Shaikh, Growth inhibition of human breast cancer cells by herbs and phytoestrogens. Oncol. Rep., 6: 1383-1387, 1999.
Foster, S., Black cohosh: *Cimicifuga racemosa*. A literature review. HerbalGram, 45: 35-49, 1999.
Fulda and Debatin, Betulinic acid induces apoptosis through a direct effect on mitochondria in neuroectodermal tumors. Med. Pediatr. Oncol., 35: 616-618, 2000.
Hall et al., The fractional inhibitory concentration (FIC) index as a measure of synergy. J. Antimicrob. Chemother., 11(5): 427-433, 1983.
Han et al., Stable overexpression of cyclin D1 in a human mammary epithelial cell line prolongs the S-phase and inhibits growth. Oncogene, 10: 953-961, 1995.
Han et al., Effects of sulindac and its metabolites on growth and apoptosis in human mammary epithelial and breast carcinoma cell lines. Breast Cancer Res. Treat., 48: 195-203, 1998.
Haridas et al., Avicins: triterpenoid saponins from *Acacia victoriae* (Bentham) induce apoptosis by mitochondrial perturbation. Proc. Natl. Acad. Sci. USA, 98: 5821-5826, 2001.
Ito et al., The novel triterpenoid CDDO induces apoptosis and differentiation of human osterosarcoma cells by a caspase-8 dependent mechanism. Mol. Pharmacol., 5: 1094-1099, 2001.
Joe et al., Cyclin D1 overexpression is more prevalent in non-Caucasian breast cancer. Anticancer Res., 21: 3535-3539, 2001.
Joe et al., Resveratrol induces growth inhibition, S-phase arrest, apoptosis, and changes in biomarker expression in several human cancer cell lines. Clin. Cancer Res., 8: 893-903, 2002.
Kruse et al., Fukic and piscidic acid esters from the rhizome of *Cimicifuga racemosa* and the in vitro estrogenic activity of fukinolic acid. Planta. med., 65: 763-764, 1999.
Lehmann-Willenbrock and Riedel, Clinical and endocrinologic studies of the treatment of ovarian insufficiency manifestations following hysterectomy with intact adnexa. Zent. BI. Gynakol., 110: 611-618, 1988.

(Continued)

*Primary Examiner*—Michele Flood
(74) *Attorney, Agent, or Firm*—Bryan Cave LLP

(57) ABSTRACT

The present invention provides a composition for use in treating or preventing neoplasia, comprising an effective actein. The present invention also provides a composition for use in treating or preventing neoplasia, comprising an effective anti-neoplastic amount of an ethyl acetate extract of black cohosh. The present invention further provides a combination of anti-neoplastic agents, comprising an effective anti-neoplastic amount of an ethyl acetate extract of black cohosh and an effective anti-neoplastic amount of at least one additional chemopreventive or chemotherapeutic agent. Methods for treating and preventing neoplasia are also provided.

9 Claims, 24 Drawing Sheets

OTHER PUBLICATIONS

Lim et al., Sulindac derivatives inhibit growth and induce apoptosis in human prostate cancer cell lines. Biochem. Pharmacol., 58: 1097-1107, 1999.

Loser et al., Inhibition of neutrophil elastase activity by cinnamic acid derivatives from *Cimicifuga racemosa*. Planta. Med., 66: 751-753, 2000.

Luo et al., PM-3, a benzo-g-pyran derivative isolated from propolis, inhibits growth of MCF-7 human breast cancer cells. Anticancer Res. 21: 1665-1672, 2001.

Masuda et al., Effects of epigallocatechin-3-gallafate on growth, epidermal growth factor receptor signaling pathways, gene expression, and chemosensitivity in human head and neck squamous cell carcinoma cell lines. Clinical Cancer Research, 7: 4220-4229, 2001.

Masuda et al., Epigallocatechin-3-gallate inhibits activation of HER-2/neu and downstream signaling pathways in human head and neck and breast carcinoma cells. Clin. Cancer Res., 9: 3486-3491, 2003.

Meiers et al., The anthocyanidins cyaniding and delphindin are potent inhibitors of the epidermal growth-factor receptor. J. Agric. Food Chem., 49: 958-962, 2001.

Nesselhut et al., Studies on mammary carcinoma cells regarding the proliferation potential of herbal medication with estrogen-like effects. Archives of Gynecology and Obstetrics, 254: 817-818, 1993.

Pedersen et al., The triterpenoid CDDO induces apoptosis in refractory CLL B cells. Blood, 8: 2965-2972, 2002.

Pisha et al., Discovery of betulinic acid as a selective inhibitor of human melanoma that functions by induction of apoptosis. Nat. Med., 1: 1046-1051, 1995.

Sakurai et al., Antitumor agents 220. Antitumor-promoting effects of cimigenol and related compounds on Epstein-Barr virus activation and two-stage mouse skin carcinogenesis. Bioorg. Med. Chem. 11: 1137-1140, 2003.

Sgambato et al., Overexpression of p27 (Kip1) inhibits the growth of both normal and transformed human mammary epithelial cells. Cancer Research, 58: 3448-3454, 1998.

Soh et al., Novel roles of specific isoforms of protein kinase C in activation of the c-fos serum response element. Molecular and Cellular Biology, 19: 1313-1324, 1999.

Soh et al., Cyclic GMP mediates apoptosis induced by sulindac derivatives via activation of c-Jun NH2-terminal kinase 1. Clin. Cancer Res., 10: 4136-4141, 2000.

Soriano et al., Synergistic effects of new chemoprotective agents and conventional cytotoxic agents against human lung cancer cell lines. Cancer Res., 59: 61, 78-84, 1999.

Sporn and Suh, Chemoprevention of Cancer. Carcinogenesis, 21: 525-530, 2000.

Stadheim et al., The novel triterpenoid 2-cyano-3,12-dioxooleana-1, 9-dien-28-oic acid (CDDO) potently enhances apoptosis induced by tumor necrosis factor in human leukemia cells. J. Biol. Chem., 19: 16448-16455, 2002.

Stoll, W., Phytotherapy influences atrophic vaginal epithelium: double-blind study—cimicifuga vs. estrogenic substances. Therapeuticum, 1: 23-31, 1987.

Suh et al., Novel triterpenoids suppress inducible nitric oxide synthase (iNOS) and inducible cyclooxygenase (COX-2) in mouse macrophages. Cancer Res., 58: 717-723, 1998.

Suh et al., A novel synthetic oleanane triterpenoid, 2-cyano-3,12-dioxoolean-1,9-dien-28-oic acid, with potent differentiating, antiproliferative, and anti-inflammatory activity. Cancer Res., 59: 336-341, 1999.

Suzui et al., Growth inhibition of human hepatoma cells by acyclic retinoid is associated with induction of p21 (CIP1) and inhibition of expression of cyclin D1. Cancer Research, 62: 3997-4006, 2002.

Tsutsui et al., Prognostic value of c-erbB2 expression in breast cancer. J. Surg. Oncol., 79:216-233, 2002.

Wang et al., A synthetic triterpenoid, 2-cyano-2,12-dioxooleana-1,9-dien-28-oic acid (CDDO), is a ligand for the peroxisome proliferators-activated receptor gamma. Mol. Endocrinol., 14: 1550-1556, 2000.

Watanabe et al., Cycloartane glycosides from the rhizomes of *Cimicifuga racemosa* and their cytotoxic activities. Chem. Pharm. Bull., 50: 121-125, 2002.

Weinstein, I. B., Disorders in cell circuitry during multistage carcinogenesis: the role of homeostasis. Carcinogenesis, 5: 857-864, 2000.

Zheng et al., Cimipure (*Cimicifuga racemosa*): a standardized black cohosh extract with novel triterpene glycoside for menopausal women. In Phytochem. Phytopharm., Shahidi and Ho, eds. (Champaign, IL: AOCS Press, 2000) pp. 360-370.

Boik J., Natural Compounds in Cancer Therapy. Oregon Medical Press: Princeton, 2001.

Baselga J., et al., Recombinant humanized anti-HER2 antibody (Herceptin) enhances the antitumor activity of paclitaxel and doxorubicin against HER2/neu overexpressing human breast cancer xenografts. Cancer Res. 58: 2825-2831, 1998.

Davis V., et al., Effects of black cohosh on mammary tumor development and progression in MMTV-neu transgenic mice. American Association for Cancer Research, vol. 44, 2nd ed., Jul. 2003 (Abstract No. R910).

Dog, TL: Black Cohosh. 2000 In: 7th Annual Course Botanical Medicine in Modern Clinical Practice, New York, May 20-24, 2002, p. 556.

Goluboff ET, et al., Exisulind (sulindac sulfone) suppresses growth of human prostate cancer in a nude mouse xenograft model by increasing apoptosis. Urology, 53: 440-444, 1999.

Hsu H-Y, et al., Oriental Materia Medica: A concise Guide. Keats Publishing, Inc., New Canaan, 1986.

Kellof GJ, et al., Cancer chemoprevention: progress and promise. Eur. J. Cancer, 14: 2031-2038, 1999.

Kennelly EJ, et al., Introduction of quinine reductase by withanolides isolated from *Physalis philadelphia* (*tomatillos*). J. Agric. Food Chem., 45: 3771-3777, 1997.

Liske E. Therapeutic efficacy and safety of *Cimicifuga racemosa* for gynecologic disorders. Adv. Nat. Ther., 15: 45-52, 1998.

Nesselhut T., Antitumor use of an extract from *Cimicifuga racemosa*. Patent Assignee: Schaper und Bruemmer G. m. b. H. un Co. K.-G., Germany, 1996.

Rockwell S., The herbal medicine black cohosh alters the response of breast cancer cells to some agents used in cancer therapy. American Association for Cancer Research, vol. 44, 2nd ed., Jul. 2003 (Abstract No. 2721).

Shirin H., et al., Antiproliferative effects of S-allylmercaptocysteine on colon cancer cells, when tested alone or in combination with sulindac sulfide. Cancer Res., 61: 725-731, 2001.

Upton R: Black Cohosh Rhizome. In: American Herbal Pharamacoeia and Therapeutic Compendium. American Herbal Pharmacopoeia, Santa Cruz, 2002.

Yoon JT., et al., CP 248, a derivative of exisulind, caused growth inhibition, mitotic arrest, and abnormalities in microtubule polymerization in glioma cells. Mol. Cancer Ther., 6: 393-404, 2002.

Zhang QW, et al., A new cycloartane saponin from *Cimicifuga acerina*. J. Asian Nat. Prod. Res., 2: 45-49, 1999.

He, K. et al., "Direct Analysis and Identification of Triterpene Glycosides by LC/MS in Black Cohosh, *Cimicifuga racemosa*, and in Several Commercially Available Black Cohosh Products", Planta Medica, 66(7):635-640 (2000).

* cited by examiner

| 26 hrs | ug/ml | viable |
|---|---|---|
| DMSO | | 1.00 |
| ac20 | 20 | 0.89 |
| ac40 | 40 | 0.30 |
| butanol 20 | 20 | 0.21 |
| 96 hrs | | viable |
| DMSO | | 1.00 |
| ETOAc | 12.5 | 0.64 |
| H2OMeOH | 12.5 | 0.91 |
| MHP20 | 12.5 | 0.86 |
| AM HP20 | 12.5 | 0.94 |
| Ac | 12.5 | 0.80 |
| ac | 6.25 | 1.15 |

FIG. 11

ANTI-NEOPLASTIC COMPOSITIONS COMPRISING EXTRACTS OF BLACK COHOSH

RELATED APPLICATIONS

This application claims the benefit of U.S. Provisional Application Ser. No. 60/437,159, filed on Dec. 27, 2002, and entitled "ANTICANCER COMPOSITIONS OF EXTRACTS OF BLACK COHOSH", the contents of which are hereby incorporated by reference herein.

STATEMENT OF GOVERNMENT INTEREST

This invention was made with government support under NIH Grant No. 3P50 AT 00090-02S2. As such, the United States Government has certain rights in this invention.

BACKGROUND OF THE INVENTION

Black cohosh, *Actaea racemosa* L. (*Cimicifuga racemosa*), a perennial in the buttercup family (Ranunculaceae), is frequently used to treat gynecological and other conditions. In particular, the roots and rhizomes of black cohosh have been used to treat a variety of disorders, including inflammatory conditions, diarrhea, dysmenorrhea, and rheumatism; they have also been used to stimulate menstrual flow and to suppress coughs (Foster, S., Black cohosh: *Cimicifuga racemosa*. A literature review. *HerbalGram*, 45:35-49, 1999).

Additionally, black cohosh has been used as a natural alternative to hormone-replacement therapy. In fact, American women are increasingly turning to black cohosh as a "more natural" alternative to estrogen, in the belief that it has the benefits, without the risks, of estrogen-replacement therapy. To date, a standardized black cohosh extract (Remifemin), developed in Germany, has been studied, both in animals and in short-term clinical trials of menopausal women. These studies suggest that the extract alleviates a variety of menopausal symptoms, particularly hot flashes (Lehmann-Willenbrock and Riedel, Clinical and endocrinological examinations concerning therapy of climacteric symptoms following hysterectomy with remaining ovaries. *Zent. Bl. Gynakol.*, 110:611-18, 1988; Stoll, W., Phytotherapy influences atrophic vaginal epithelium: double-blind study—*cimicifuga* vs. estrogenic substances. *Therapeuticum*, 1:23-31, 1987). Although most studies report that black cohosh is free of significant side-effects, these studies have not been carried out for a length of time sufficient to ensure the safety of black cohosh with respect to uterine function and/or the induction or stimulation of breast cancer growth. Since the population using black cohosh (i.e., middle-aged females in developed countries) is at a higher risk for breast cancer, research is needed to clarify whether black cohosh extracts stimulate or inhibit breast cancer cells. Such studies could also identify new approaches to breast cancer prevention and treatment.

The components of the black-cohosh rhizome have been examined in several studies. It is known that the rhizome contains triterpene glycosides, aromatic acids, cinnaminic acid esters, sugars, tannins, and long-chain fatty acids (Zheng et al., CimiPure (*Cimicifuga racemosa*): a standardized black cohosh extract with novel triterpene glycoside for menopausal women. In *Phytochem. Phytopharm.*, Shahidi and Ho, eds. (Champaign, Ill.: AOCS Press, 2000) pp. 360-70). However, little is known about the mechanisms by which these compounds are metabolized in vivo.

Crude extracts of black cohosh, and several components present in black cohosh, have been shown to exhibit biological activity. Fukinolic acid (2-E-caffeoylfukiic acid) exhibited weak estrogenic activity on MCF7 cells (Kruse et al., Fukic and piscidic acid esters from the rhizome of *Cimicifuga racemosa* and the in vitro estrogenic activity of fukinolic acid. *Planta. Med.*, 65:763-64, 1999); it also inhibited the activity of neutrophil elastase, which is involved on the inflammatory process (Loser et al., Inhibition of neutrophil elastase activity by cinnamic acid derivatives from *Cimicifuga racemosa*. *Planta. Med.*, 66:751-53, 2000). Bioactivity-guided fractionation of the methanolic extract resulted in the isolation of nine antioxidant compounds. Of these, methyl caffeate was the most active in reducing menadione-induced DNA damage in cultured S30 breast cancer cells (Burdette et al., Black cohosh (*Cimicifuga racemosa* L.) protects against menadione-induced DNA damage through scavenging of reactive oxygen species: bioassay-directed isolation and characterization of active principles. *J. Agric. Food Chem.*, 50:7022-28, 2002). None of the compounds was cytotoxic to S30 cells (Burdette et al., Black cohosh (*Cimicifuga racemosa* L.) protects against menadione-induced DNA damage through scavenging of reactive oxygen species: bioassay-directed isolation and characterization of active principles. *J. Agric. Food Chem.*, 50:7022-28, 2002).

Extracts and components purified from black cohosh have also been shown to exhibit anti-cancer activity, in vitro and in vivo. Extracts of black cohosh (ethanol extract, 0.1% v/v) inhibited the growth of serum-stimulated T-47D breast cancer cells (Dixon-Shanies and Shaikh, Growth inhibition of human breast cancer cells by herbs and phytoestrogens. *Oncol. Rep.*, 6:1383-87, 1999), and, at doses starting at 2.5 µg/ml, inhibited the proliferation of the mammary carcinoma cell line, 435 (Nesselhut et al., Studies on mammary carcinoma cells regarding the proliferation potential of herbal medication with estrogen-like effects. *Archives of Gynecology and Obstetrics*, 254:817-18, 1993). Furthermore, isopropanolic extracts of black cohosh inhibited estrogen-induced proliferation of MCF7 cells, and enhanced the inhibitory effect of tamoxifen (Bodinet and Freudenstein, Influence of *Cimicifuga racemosa* on the proliferation of estrogen receptor-positive human breast cancer cells. *Breast Cancer Research and Treatment*, 76:1-10, 2002).

More recently, it has been shown that cycloartane glycosides isolated from black cohosh inhibit the growth of human oral squamous cell carcinoma cells (Watanabe et al., Cycloartane glycosides from the rhizomes of *Cimicifuga racemosa* and their cytotoxic activities. *Chem. Pharm. Bull.*, 50:121-25, 2002). Additionally, recent studies by Sakurai et al. have indicated that triterpene glycosides and aglycones—the most active of which is cimigenol—inhibit Epstein-Barr virus early antigen activation (induced by 12-O-tetradecanoylphorbol-13-acetate) in Raji cells (Sakurai et al., Antitumor agents 220. Antitumor-promoting effects of cimigenol and related compounds on Epstein-Barr virus activation and two-stage mouse skin carcinogenesis. *Bioorg. Med. Chem.* 11:1137-40, 2003). Cimigenol has also been shown to inhibit mouse skin tumor promotion using DMBA as an initiator and TPA as a promoter.

All of the foregoing studies, however, have been limited in scope, and have not addressed issues of specificity and mechanism of action.

SUMMARY OF THE INVENTION

The invention disclosed herein generally relates to the effects of extracts of black cohosh on the growth and progression of the cell cycle, and on the expression of proteins involved in cell-cycle control in cancer-cell lines. More particularly, the present invention relates to the effects of actein and triterpene-glycoside extracts of black cohosh on neoplastic cells—when used alone or in combination with a chemopreventive or chemotherapeutic agent.

Accordingly, in one aspect, the present invention provides a composition for use in treating or preventing neoplasia, comprising an effective anti-neoplastic amount of an ethyl acetate extract of black cohosh.

In another aspect, the present invention provides a combination of anti-neoplastic agents, comprising an effective anti-neoplastic amount of an ethyl acetate extract of black cohosh and an effective anti-neoplastic amount of at least one additional chemopreventive or chemotherapeutic agent. In one embodiment of the invention, the combination is a synergistic combination.

In a further aspect, the present invention provides a composition for use in treating or preventing neoplasia, comprising an effective anti-neoplastic amount of actein. In one embodiment, the composition further comprises an effective anti-neoplastic amount of at least one additional chemopreventive or chemotherapeutic agent.

In yet another aspect, the present invention provides a method for treating or preventing neoplasia in a subject, by administering to the subject an amount of an ethyl acetate extract of black cohosh effective to treat or prevent the neoplasia.

In still another aspect, the present invention provides a method for treating or preventing neoplasia in a subject, by administering to the subject an amount of an ethyl acetate extract of black cohosh effective to treat or prevent the neoplasia, in combination with an amount of at least one additional chemopreventive or chemotherapeutic agent effective to treat or prevent the neoplasia. In one embodiment of the invention, a synergistic anti-neoplastic effect results.

Furthermore, the present invention provides a method for treating or preventing neoplasia in a subject, comprising administering to the subject an amount of actein effective to treat or prevent the neoplasia. In one embodiment, the method further comprises administering to the subject an amount of at least one additional chemopreventive or chemotherapeutic agent effective to treat or prevent the neoplasia.

Additional aspects of the present invention will be apparent in view of the description that follows.

BRIEF DESCRIPTION OF THE FIGURES

FIG. 2A shows the effect of the ethyl acetate extract when MCF7 cells were treated with the indicated concentrations of the ethyl acetate fraction for increasing times. FIG. 2B shows the effect of actein when MCF7 cells were treated with the indicated concentrations of actein for increasing times. In each case, the number of viable cells was determined using a Coulter Counter, and the control contained 0.08% DMSO. Bars=SD

FIG. 11 shows the effects of butanol fractions from black cohosh on cell proliferation in MCF7 cells. MCF7 cells were exposed to increasing concentrations of the indicated purified components, for 26 or 96 h, and the number of viable cells was determined using a Coulter Counter.

DETAILED DESCRIPTION OF THE INVENTION

Figure 1:
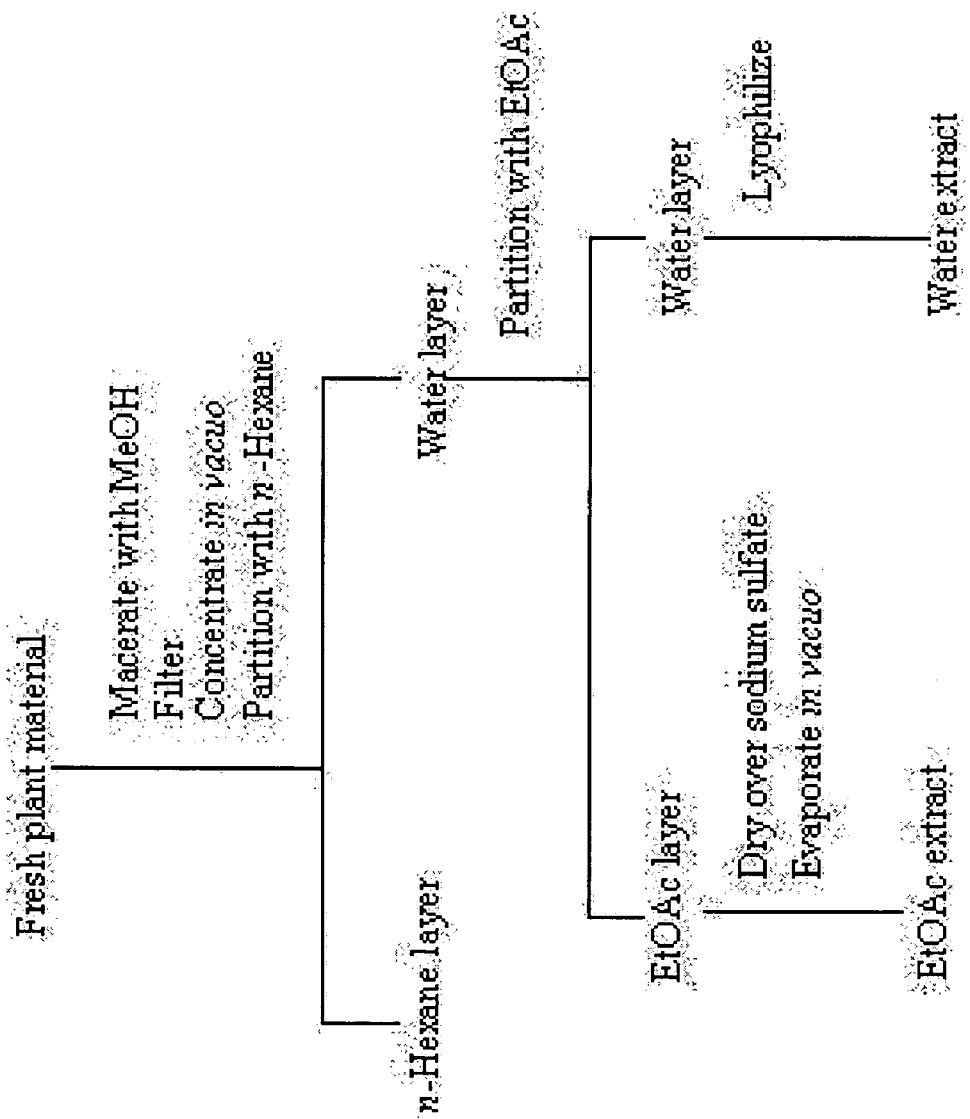
FIG. 1 is an illustration of the methods of the invention which were used to fractionate black cohosh.

The Examples below provide the first detailed examination of the effects on human breast cancer cells of extracts and purified compounds present in black cohosh. In these studies, the roots and rhizomes of black cohosh were extracted with MeOH/$H_2O$, and fractionated by solvent-solvent partitioning to yield three fractions: hexane, ethyl acetate (EtOAc), and $H_2O$. The EtOAc fraction exhibited the greatest growth-inhibitory activity. This fraction inhibited growth of both the $ER^+$ MCF7 and $ER^-$/Her2+MDA-MB-453 human breast cancer cell lines, with $IC_{50}$ values of about 18 µg/ml and 10 µg/ml, respectively. The normal human mammary epithelial cell line, MCF10F, was much less sensitive to growth inhibition by this extract (with an $IC_{50}$ value of 46 µg/ml). It is possible that the greater sensitivity of the malignant cells may reflect, in part, the difference in growth rates of the malignant and non-malignant cells.

The inventors tested the effects of crude extracts, methanol and ethanol, as well as ethanol extracts provided by Pure World, native and plus expedient: the $IC_{50}$ values for these extracts after 96 hours of treatment were: methanol: 100 µg/ml; ethanol: >200 µg/ml; Pure World native: 175 µg/ml; and Pure World plus expedient: 195 µg/ml. To partition the phytochemicals according to polarity, the water portion was also partitioned sequentially with hexane and n-butanol (n-BuOH). The n-BuOH fraction was tested for its effect on the growth of MDA-MB-453 breast cancer cells. The IC50 value after 96 hours of treatment was: 40 µg/ml.

The inventors also examined the effects of the EtOAc fraction of black cohosh on SW480 human colon cancer cells. The IC50 values after 48 hours of incubation using the MTT assay were: SW480: 42 µg/ml; MCF7: 38 µg/ml (Luo et al., PM-3, a benzo-g-pyran derivative isolated from propolis, inhibits growth of MCF-7 human breast cancer cells. *Anticancer Res* 21: 1665-1672, 2001).

The inventors further demonstrated that the EtOAc fraction of black cohosh induced cell-cycle arrest in MCF7 human breast cancer cells at G1 at 30 µg/ml, and at G2/M at 60 µg/ml. The triterpene glycoside fraction that was obtained by polyamide column chromatography, and the specific triterpene glycosides (actein, 23-epi-26-deoxyactein, and cimiracemoside A), inhibited growth of MCF7 human breast cancer cells and induced cell-cycle arrest at G1. At 60 µg/ml, actein induced a less-pronounced G1 arrest. Therefore, it is likely that, at high concentrations, actein and related compounds affect proteins that regulate later phases in the cell cycle.

Because the triterpene glycosides induced cell-cycle arrest at G1, the inventors decided to ascertain the effect of the most potent compound, actein, on cell-cycle proteins that control G1 cell-cycle progression. As discussed below, actein decreased the level of cyclin D1, cdk4, and the hyperphosphorylated form of pRb, and increased the level of the cdk inhibitory protein, $p21^{cip1}$, in MCF7 cells—changes that may contribute to the arrest in G1. The inventors also found that actein reduced the level of cyclin D1 mRNA within 3 h of treatment, and significantly reduced the level at 24 h, suggesting an effect at the level of transcription. The level of the EGFR was not altered after treatment with actein; nor was there a consistent effect on the level of the phosphorylated form of the EGFR (p-EGFR), which reflects its state of activation. Thus, the EGFR did not appear to be a direct target for actein. This result is in contrast to the effect of another plant-derived compound—a flavonol, epigallocatechin-gallate—which is the active component in green tea (Masuda et al., Effects of epigallocatechin-3-gallate on growth, epidermal growth factor receptor signaling pathways, gene expression, and chemosensitivity in human head and neck squamous cell carcinoma cell lines. *Clinical Cancer Research*, 7:4220-29, 2001). Previous studies have also indicated that micromolar concentrations of the aglycone compounds, cyanidin and delphinidin, inhibited activation of the EGFR and cell proliferation in the human vulva carcinoma cell line, A431, whereas the corresponding glycosides had a minimal effect (Meiers et al., The anthocyanidins cyanidin and delphinidin are potent inhibitors of the epidermal growth-factor receptor. *J. Agric. Food Chem*., 49:958-62, 2001). The inventors tested the effects of the aglycone cimigenol on the growth of human breast cancer cells. Cimigenol was less active than cimigenol glycoside.

Triterpene molecules are structurally related to steroids, and have been present in the plant kingdom for millions of years. Some may have evolved to become ligands for receptors on animal cells (Sporn and Suh, Chemoprevention of cancer. *Carcinogenesis*, 21:525-30, 2000). However, the mode of action triterpene glycosides is not well understood. Studies by Haridas et al. (Avicins: triterpenoid saponins from *Acacia victoriae* (Bentham) induce apoptosis by mitochondrial perturbation. *Proc. Natl. Acad. Sci. USA*, 98:5821-26, 2001) indicate that avicins—triterpenoid saponins from the plant *Acacia victoriae* (Bentham)—are potent inhibitors of the transcription factor, nuclear factor kappa B (NF-κB), and act by inhibiting its translocation to the nucleus and its capacity to bind DNA—perhaps by altering sulfhydryl groups critical for NF-κB activation. Betulinic acid, a pentacyclic triterpene present in the bark of white birch trees, is a selective inhibitor of human melanoma (Pisha et al., Discovery of betulinic acid as a selective inhibitor of human melanoma that functions by induction of apoptosis. *Nat. Med.*, 1:1046-51, 1995). It induces apoptosis in neuroectodermal tumors by a direct effect on mitochondria (Fulda and Debatin, Betulinic acid induces apoptosis through a direct effect on mitochondria in neuroectodermal tumors. *Med. Pediatr. Oncol.*, 35:616-18, 2000).

Suh et al. (Novel triterpenoids suppress inducible nitric oxide synthase (iNOS) and inducible cyclooxygenase (COX-2) in mouse macrophages. *Cancer Res.*, 58:717-23, 1998) have generated a series of derivatives of the triterpenes, oleanic and ursolic acids, that are highly potent in suppressing the expression of inducible nitric oxide synthase and cyclooxygenase-2 in primary mouse macrophages. Indeed, the derivative, 2-cyano-3,12-dioxooleana-1,9-dien-28-oic acid (CDDO), is 1000 times more potent than oleanic acid in this cell system (Sporn and Suh, Chemoprevention of cancer. *Carcinogenesis*, 21:525-30, 2000). Suh et al. also found that CDDO displays potent differentiating, anti-proliferative, and anti-inflammatory activities (Suh et al., A novel synthetic oleanane triterpenoid, 2-cyano-3,12-dioxoolean-1,9-dien-28-oic acid, with potent differentiating, antiproliferative, and anti-inflammatory activity. *Cancer Res.*, 59:336-41, 1999).

CDDO further induces apoptosis by a caspase-8-dependent mechanism (Ito et al., The novel triterpenoid CDDO induces apoptosis and differentiation of human osteosarcoma cells by a caspase-8 dependent mechanism. *Mol. Pharmacol.*, 5:1094-99, 2001; Pedersen et al., The triterpenoid CDDO induces apoptosis in refractory CLL B cells. *Blood*, 8:2965-72, 2002), and inhibits NF-κB-mediated gene expression, following translocation of the activated form to the nucleus (Stadheim et al., The novel triterpenoid 2-cyano-3,12-dioxooleana-1,9-dien-28-oic acid (CDDO) potently enhances apoptosis induced by tumor necrosis factor in human leukemia cells. *J. Biol. Chem.*, 19:16448-55, 2002). It is a ligand for the peroxisome proliferator activated receptor-γ (PPAR-γ) (Wang et al., A synthetic triterpenoid, 2-cyano-2,12-dioxooleana-1,9-dien-28-oic acid (CDDO), is a ligand for the peroxisome proliferator-activated receptor gamma. *Mol. Endocrinol.*, 14:1550-56, 2000), but the specific cellular target of CDDO and related compounds, for mediating the above biologic effects, is not known.

The triterpene glycoside, actein, and the fraction of black cohosh enriched for triterpene glycosides (which are selective for human breast cancer versus normal mammary epithelial cells), synergize with several classes of chemotherapy agents. For example, the inventors have demonstrated that actein has synergy with the taxane, paclitaxel; the antimetabolite, 5-flourouracil (5-FU); the Her2 antibody, herceptin; the anthracycline antibiotic, doxorubicin; and the platinum analog, cisplatin. Additionally, the inventors have shown that black cohosh extracts have synergy with paclitaxel and doxorubicin. Because it is easier to prepare enriched extracts, the extracts of black cohosh might represent the preferred sources to be used in combination with such chemotherapeutic agents.

In view of the foregoing, the present invention provides methods for treating and preventing neoplasia in a subject. The subject is preferably a mammal (e.g., humans, domestic animals, and commercial animals, including cows, dogs, monkeys, mice, pigs, and rats). More preferably, the subject is a human.

As used herein, "neoplasia" refers to the uncontrolled and progressive multiplication of cells under conditions that would not elicit, or would otherwise cause cessation of, the multiplication of normal or non-neoplastic cells. Neoplasia results in the formation of a neoplasm, which is any new and abnormal growth, particularly a new growth of tissue, in which the growth is uncontrolled and progressive. Malignant neoplasms are distinguished from benign in that the former show a greater degree of anaplasia, or loss of differentiation and orientation of cells, and have the properties of invasion and metastasis. Thus, neoplasia includes "cancer", which refers herein to a proliferation of cells having the unique trait of loss of normal controls, resulting in unregulated growth, lack of differentiation, local tissue invasion, and metastasis (Beers and Berkow, eds., *The Merck Manual of Diagnosis and Therapy*, 17$^{th}$ ed. (Whitehouse Station, N.J.: Merck Research Laboratories, 1999) 973-74, 976, 986, 988, 991).

Neoplasias which may be treated and/or prevented by the methods of the present invention include, without limitation, carcinomas, particularly those of the bladder, breast, cervix, colon, head, kidney, lung, neck, ovary, prostate, and stomach; lymphocytic leukemias, particularly acute lymphoblastic leukemia and chronic lymphocytic leukemia; myeloid leukemias, particularly acute monocytic leukemia, acute promyelocytic leukemia, and chronic myelocytic leukemia; malignant lymphomas, particularly Burkitt's lymphoma and Non-Hodgkin's lymphoma; malignant melanomas; myeloproliferative diseases; sarcomas, particularly Ewing's sarcoma, hemangiosarcoma, Kaposi's sarcoma, liposarcoma, peripheral neuroepithelioma, and synovial sarcoma; and mixed types of neoplasias, particularly carcinosarcoma and Hodgkin's disease. Preferably, the methods of the present invention are used to treat or prevent breast cancer, colon cancer, leukemia, lung cancer, malignant melanoma, ovarian cancer, or prostate cancer. More preferably, the cancer is breast cancer.

The method of the present invention comprises administering to the subject an ethyl acetate extract of black cohosh or a composition comprising actein. It is well known that black cohosh is a medicinal plant from the genus *Cimicifuga* (or *Actea*) and the species racemosa. The ethyl acetate extract of black cohosh is a partially-purified extract, enriched for triterprene glycosides. It is a safe and effective extract, with few side effects. The ethyl acetate extract of black cohosh may be prepared in any suitable manner that maintains or enriches the triterpene glycosides component in the extract. By way of example, the method of extraction may comprise a first extraction of the rhizome of black cohosh, with an aqueous solution of a lower alkyl alcohol, followed by partitioning of the aqueous alcohol layer with a lower alkyl acetate. A preferred lower alkyl alcohol is methanol, and a preferred lower alkyl acetate is ethyl acetate. The resultant extract comprises triterpene glycoside compounds and cinnamic acid esters. Of interest to the invention are the triterpene glycosides, which can be separated from the cinnamic acid esters by purification of the ethyl acetate extract. Such triterpene glycosides include, without limitation, actein, cimifugoside, cimigenol glycoside, cimiracemoside A, 23-epi-26-deoxyactein and the aglycone cimigenol. Preferably, the triterpene glycoside compound is actein.

The individual triterpenoid components in the ethyl acetate extract of black cohosh can be individually separated by purification. The ethyl acetate extract may be maintained in any form, provided that the activity of the triterpene glycosides, and of each component therein, is maintained. Activity of the triterpene glycosides may be assayed by reference to the Examples presented below. Furthermore, actein and related triterprene glycosides may be modified to increase their activity, while retaining their selectivity for neoplastic cells.

In accordance with the method of the present invention, the ethyl acetate extract of black cohosh may be administered to the subject in an anti-neoplastic amount, which is an amount that is effective to treat or prevent neoplasia in the subject. As used herein, "anti-neoplastic" includes the ability to inhibit or prevent the development or spread of a neoplasm, and the ability to limit, suspend, terminate, or otherwise control the development, maturation, and proliferation of cells in a neoplasm. As further used herein, an amount of the ethyl acetate extract of black cohosh that is "effective to treat or prevent the neoplasia" is an amount that is effective to ameliorate or minimize the clinical impairment or symptoms of the neoplasia, or to inhibit their development. For example, the clinical impairment or symptoms of the neoplasia may be ameliorated or minimized by diminishing any pain or discomfort suffered by the subject; by extending the survival of the subject beyond that which would otherwise be expected in the absence of such treatment; by inhibiting or preventing the development or spread of the neoplasm; or by limiting, suspending, terminating, or otherwise controlling the development, maturation, and proliferation of cells in the neoplasm.

Exemplary doses of actein, administered intraperitoneally, may be between about 0.5 µg/ml and about 40.0 µg/ml, and preferably, between about 1 µg/ml and about 3.0 µg/ml. However, the amount of actein effective to treat or prevent neoplasia or other disorders in a subject will vary depending on the particular factors of each case, including the target molecule, the type of neoplasia, the stage of neoplasia, the subject's weight, the severity of the subject's condition, and the method of administration. These amounts can be readily determined by the skilled artisan, based upon known procedures, including analysis of titration curves established in vivo, dose-response experiments analogous to those provided in the Examples, and methods and assays disclosed herein.

The ethyl acetate extract of black cohosh or the actein composition may be administered to a human or animal subject by known procedures, including, without limitation, oral administration, parenteral administration, transdermal administration, and by way of catheter. Preferably, the ethyl acetate extract of black cohosh or the actein composition is administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual injection.

For oral administration, a formulation comprising the ethyl acetate extract of black cohosh or the actein composition may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, and gelatins. Additionally, the formulation may be presented with disintegrators, such as corn starch, potato starch, and sodium carboxymethylcellulose. The formulation also may be presented with dibasic calcium phosphate anhydrous or sodium starch glycolate. Finally, the formulation may be presented with lubricants, such as talc and magnesium stearate.

For parenteral administration (i.e., administration by injection through a route other than the alimentary canal), the ethyl acetate extract of black cohosh or the actein composition may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, and sublingual.

For transdermal administration, the ethyl acetate extract of black cohosh or the actein composition may be combined with skin penetration enhancers, such as propylene glycol, polyethylene glycol, isopropanol, ethanol, oleic acid, N-methylpyrrolidone, and the like, which increase the permeability of the skin to the ethyl acetate extract of black cohosh, and permit the ethyl acetate extract of black cohosh to penetrate through the skin and into the bloodstream. The ethyl acetate extract of black cohosh, or the actein composition, /enhancer composition also may be further combined with a polymeric substance, such as ethylcellulose, hydroxypropyl cellulose, ethylene/vinylacetate, polyvinyl pyrrolidone, and the like, to provide the composition in gel form, which may be dissolved in a solvent, such as methylene chloride, evaporated to the desired viscosity, and then applied to backing material to provide a patch.

In accordance with the method of the present invention, the ethyl acetate extract of black cohosh or the actein composition also may be administered to a subject by way of a pharmaceutical composition for use in treating or preventing neoplasia. The pharmaceutical composition of the present invention comprises an effective anti-neoplastic amount of the ethyl acetate extract of black cohosh or an effective amount of the actein composition and a pharmaceutically-acceptable carrier. The pharmaceutically-acceptable carrier must be "acceptable" in the sense of being compatible with the other ingredients of the composition, and not deleterious to the recipient thereof. The pharmaceutically-acceptable carrier employed herein is selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

In the pharmaceutical composition of the present invention, the ethyl acetate extract of black cohosh is provided in an effective anti-neoplastic amount. For example, where the ethyl acetate extract comprises actein, the actein may be present in an amount between about 0.5 µg/ml and about 40.0 µg/ml. Preferably, the actein is present in an amount between about 1.0 µg/ml and about 3.0 µg/ml.

The pharmaceutical composition of the present invention may be prepared by methods well-known in the pharmaceutical arts. Actein may be obtained from plant extracts or by chemical synthesis. For example, the ethyl acetate extract of black cohosh may be brought into association with a carrier or diluent, as a suspension or solution. Optionally, one or more accessory ingredients (e.g., buffers, flavoring agents, surface active agents, and the like) also may be added. The choice of carrier will depend upon the route of administration.

Since multiple genetic and epigenetic targets are altered in the process of carcinogenesis, combination chemoprevention and chemotherapy are generally optimal. Accordingly, the present invention further provides a method for treating or preventing neoplasia in a subject, by administering to the subject an amount of an ethyl acetate extract of black cohosh or the actein composition, as described above, in combination with an amount of at least one additional chemopreventive or chemotherapeutic agent effective to treat or prevent the neoplasia. As used herein, the term "effective" also covers the dosages at which the chemopreventive or chemotherapeutic agent by itself does not have any significant effect on neoplasia but may significantly promote or enhance the anti-neoplastic effects of the ethyl acetate extract of black cohosh, and vice-versa.

Examples of additional chemopreventive or chemotherapeutic agents for use in the method of the present invention include, without limitation cisplatin, docetaxel, doxorubicin, 5-fluorouracil (5-FU), herceptin, paclitaxel, tamoxifen, and vinblastine, and any fragments, analogues, and derivatives thereof. In a preferred embodiment, the chemopreventive or chemotherapeutic agent is paclitaxel. Ethyl acetate extracts of black cohosh, and additional chemopreventive or chemotherapeutic agents, are referred to herein as "anti-neoplastic agents."

By way of example, the term "paclitaxel" includes a natural or synthetic functional variant of paclitaxel which has paclitaxel biological activity, as well as a fragment of paclitaxel having paclitaxel biological activity.

As used herein, the term "paclitaxel biological activity" refers to paclitaxel activity which interferes with cellular mitosis by affecting microtubule formation and/or action, thereby producing antimitotic and anti-neoplastic effects. Methods of preparing paclitaxel and its analogues and derivatives are well-known in the art, and are described, for example, in U.S. Pat. Nos. 5,569,729; 5,565,478; 5,530,020; 5,527,924; 5,484,809; 5,475,120; 5,440,057; and 5,296,506. Paclitaxel and its analogues and derivatives are also available commercially. For example, synthetic paclitaxel can be obtained from Bristol-Myers Squibb Company, Oncology Division (Princeton, N.J.), under the registered trademark Taxol™. Moreover, paclitaxel may be synthesized in accordance with known organic chemistry procedures that are readily understood by one skilled in the art. Taxol for injection may be obtained in a single-dose vial, having a concentration of 30 mg/5 ml (6 mg/ml per 5 ml) (Physicians' Desk Reference, $54^{th}$ ed. (Montvale, N.J.: Medical Economics Company, Inc., 2000) 307, 682).

Paclitaxel and its analogues and derivatives have been used successfully to treat leukemias and tumors. In particular, paclitaxel is useful in the treatment of breast, lung, and ovarian cancers. Since paclitaxel is frequently utilized in the treatment of human cancers, a strategy to enhance its utility in the clinical setting, by combining its administration with that of an ethyl acetate extract of black cohosh, may be of great benefit to many subjects suffering from malignant neoplasias, particularly advanced cancers.

In the method of the present invention, administration of an ethyl acetate extract of black cohosh "in combination with" one or more additional chemopreventive or chemotherapeutic agents refers to co-administration of the anti-neoplastic agents. Co-administration may occur concurrently, sequentially, or alternately. Concurrent co-administration refers to administration of the anti-neoplastic agents at essentially the same time. For concurrent co-administration, the courses of treatment with the ethyl acetate extract of black cohosh, and with the one or more additional chemopreventive or chemotherapeutic agents, may be run simultaneously. For example, a single, combined formulation, containing both an amount of the ethyl acetate extract of black cohosh and an amount of the additional chemopreventive or chemotherapeutic agent, in physical association with one another, may be administered to a subject. By way of example, the single, combined formulation may consist of a liquid mixture, containing amounts of both anti-neoplastic agents, which may be injected into a subject, or an oral formulation, containing amounts of both anti-neoplastic agents, which may be orally administered to a subject.

It is also within the confines of the present invention that an amount of the ethyl acetate extract of black cohosh, and an amount of the one or more additional chemopreventive or chemotherapeutic agents, may be administered concurrently to a subject, in separate, individual formulations. Accordingly, the method of the present invention is not limited to concurrent co-administration of the anti-neoplastic agents in physical association with one another.

In the method of the present invention, the ethyl acetate extract of black cohosh, and the one or more additional chemopreventive or chemotherapeutic agents, also may be co-administered to a subject in separate, individual formulations that are spaced out over a period of time, so as to obtain the maximum efficacy of the combination. Administration of each drug may range in duration from a brief, rapid administration to a continuous perfusion. When spaced out over a period of time, co-administration of the anti-neoplastic agents may be alternate or sequential. For alternate co-administration, partial courses of treatment with the ethyl acetate extract of black cohosh may be alternated with partial courses of treatment with the one or more additional chemopreventive or chemotherapeutic agents, until a full treatment of each drug has been administered. For sequential co-administration, one of the anti-neoplastic agents is separately administered, followed by the other. For example, a full course of treatment with the ethyl acetate extract of black cohosh may be completed, and then may be followed by a full course of treatment with the one or more additional chemopreventive or chemotherapeutic agents. Alternatively, for sequential co-administration, a full course of treatment with the one or more additional chemopreventive or chemotherapeutic agents may be completed, then followed by a full course of treatment with the ethyl acetate extract of black cohosh.

The anti-neoplastic agents of the present invention (i.e., the ethyl acetate extract of black cohosh or the actein composition and the one or more additional chemopreventive or chemotherapeutic agents, either in a single, combined formulation, or in separate, individual formulations) may be administered to a human or animal subject by known procedures, including, but not limited to, oral administration, parenteral administration, and transdermal administration, as described above. Preferably, the anti-neoplastic agents of the present invention are administered orally or intravenously. For oral administration, the formulations of the ethyl acetate extract of black cohosh or the actein composition and the one or more additional chemopreventive or chemotherapeutic agents (whether individual or combined) may be presented as capsules, tablets, powders, granules, as a suspension, or in any other form described herein. For parenteral administration, the formulations of the ethyl acetate extract of black cohosh or the actein composition and the one or more additional chemopreventive or chemotherapeutic agents (whether individual or combined) may be combined with a sterile aqueous solution which is preferably isotonic with the blood of the subject. Such formulations may be prepared in accordance with methods described herein. For transdermal administration, the formulations of the ethyl acetate extract of black cohosh or the actein composition and the one or more additional chemopreventive or chemotherapeutic agents (whether individual or combined) may be combined with skin penetration enhancers, such as propylene glycol, polyethylene glycol, isopropanol, ethanol, oleic acid, N-methylpyrrolidone, and the like, and prepared in accordance with methods described herein.

Additionally, in accordance with the method of the present invention, the ethyl acetate extract of black cohosh or the actein composition and the one or more additional chemopreventive or chemotherapeutic agents are administered to a subject in amounts effective to treat or prevent neoplasia and other disorders in the subject. As discussed above, exemplary doses of actein may range from about 0.5 μg/ml to about 40.0 μg/ml; exemplary doses of paclitaxel, for example, may range from 0.5 nM to about 5.0 nM. However, the amounts of the ethyl acetate extract of black cohosh, or the actein composition, and the one or more additional chemopreventive or chemotherapeutic agents, that are effective to treat or prevent neoplasia in a subject will vary depending on the particular factors of each case, including the type and stage of disorders (e.g. neoplasia), the subject's weight, the severity of the subject's condition, and the method of administration. These amounts can be readily determined by the skilled artisan, based upon known procedures, including analysis of titration curves established in vivo, dose-response experiments analogous to those provided in the Examples, and methods and assays disclosed herein.

In one embodiment of the present invention, an ethyl acetate extract of black cohosh or the actein composition is administered to a subject in combination with at least one additional chemopreventive or chemotherapeutic agent, such that a synergistic anti-neoplastic effect is produced. As used herein, a "synergistic anti-neoplastic effect" refers to a greater-than-additive anti-neoplastic effect which is produced by a combination of two drugs, and which exceeds that which would otherwise result from individual administration of either drug alone.

In the method of the present invention, combination therapy using an ethyl acetate extract of black cohosh or the actein composition and at least one additional anti-neoplastic agent preferably results in an anti-neoplastic effect that is greater than additive, as determined by any of the measures of synergy known in the art. One measure of synergy between two drugs is the fractional inhibitory concentration (FIC) (Hall et al., The fractional inhibitory concentration (FIC) index as a measure of synergy. *J. Antimicrob. Chemother.*, 11(5):427-33, 1983). This fractional value is determined by expressing the $IC_{50}$ of a drug acting in combination, as a function of the $IC_{50}$ of the drug acting alone. For two interacting drugs, the sum of the FIC value for each drug represents the measure of synergistic interaction. Where the FIC is less than 1, there is synergy between the two drugs. An FIC value of 1 indicates an additive effect. The smaller the FIC value, the greater the synergistic interaction.

Another measurement of synergy is the combination index (CI) method of Chou and Talalay (Quantitative analysis of dose-effect relationships: the combined effects of multiple drugs or enzyme inhibitors. *Adv. Enzyme Regul.*, 22:27-55, 1984), which is based on the median-effect principle. This method calculates the degree of synergy, additivity, or antagonism between two drugs at various levels of cytotoxicity. Where the CI value is less than 1, there is synergy between the two drugs. Where the CI value is 1, there is an additive effect, but no synergistic effect. CI values greater than 1 indicate antagonism. The smaller the CI value, the greater the synergistic effect.

As the inventors have demonstrated herein, administration of an ethyl acetate extract of black cohosh, in combination with at least one additional chemopreventive or chemotherapeutic agent, frequently results (unexpectedly) in a synergistic anti-neoplastic effect, by providing greater efficacy than would result from use of either of the anti-neoplastic agents alone. In these cases, the ethyl acetate extract of black cohosh enhances the effects of the additional chemopreventive or chemotherapeutic agent; therefore, lower doses of one or both of the anti-neoplastic agents may be used in treating and preventing neoplasias, resulting in increased chemotherapeutic/chemopreventive efficacy, and decreased side-effects.

By way of example, the ethyl acetate fraction of black cohosh (2 μg/ml) may be combined with doxorubicin (0.2 μg/ml; 0.34 μM) or paclitaxel (4 nM) for a synergistic effect. Furthermore, actein (2 μg/ml; 3.0 μM) may be combined with 5-FU (0.002 μg/ml, 0.015 μM) for a synergistic effect; actein (0.2 or 2 μg/ml) may be combined with herceptin (8 μg/ml; 54 nM) for a synergistic effect; actein (1 μg/ml) may be combined with paclitaxel (1 nM) for a synergistic effect; actein (2 μg/ml; 3.0 μM) may be combined with doxorubicin (0.2 μg/ml; 0.34 μM) for a synergistic effect; actein (2 μg/ml; 2.8 μM) may be combined with tamoxifen (2 μg/ml; 5.4 μM) for a synergistic effect; actein (2 μg/ml; 3.0 μM) may be combined with cisplatin (2 μg/ml; 6.7 μM) for a synergistic effect; and actein (2 μg/ml; 3.0 μM) may be combined with vinblastine (4 μg/ml; 4.4 μM) for an additive effect. In a preferred embodiment of the present invention, actein (e.g., about 0.5 μg/ml to about 5.0 μg/ml) is administered to a subject in combination with paclitaxel (e.g., about 0.5 nM to about 5.0 nM).

As shown herein, administration of the ethyl acetate extract of black cohosh (particularly the extract containing one or more triterpene glycosides, such as actein, cimifugoside, cimigenol glycoside, cimiracemoside A, and 23-epi-26-deoxyactein), or the actein composition, in combination with one or more additional chemopreventive or chemotherapeutic agents (particularly the anti-neoplastic agents, cisplatin, docetaxel, doxorubicin, 5-fluorouracil, herceptin, paclitaxel, tamoxifen, and vinblastine), may unexpectedly result in a synergistic anti-neoplastic effect by providing greater efficacy than would result from use of either of the anti-neoplastic agents alone. Accordingly, it is also within the confines of the present invention that a formulation of the ethyl acetate extract of black cohosh or the actein composition and a formulation of the one or more additional chemopreventive or chemotherapeutic agents (whether individual or combined) may be further associated with a pharmaceutically-acceptable carrier, thereby comprising a combination of anti-neoplastic agents. In one embodiment of the invention, the combination of anti-neoplastic agents is a synergistic combination. As used herein, a "synergistic combination" of anti-neoplastic agents refers to a combination of anti-neoplastic agents that achieves a greater anti-neoplastic effect than would otherwise result if the anti-neoplastic agents were administered individually.

The formulations of the combination of the present invention may be prepared by methods well-known in the pharmaceutical arts and described herein. Exemplary acceptable pharmaceutical carriers have been discussed above. An additional carrier, Cremophor™, may be useful, as it is a common vehicle for Taxol.

In the combination of the present invention, the relative proportions of the ethyl acetate extract of black cohosh (including the triterpene glycoside compounds) or the actein composition and the one or more chemopreventive or chemotherapeutic agents will depend on the specific application of the combination. Thus, while certain proportions may be beneficial in treating one type of tumor, entirely different proportions may be beneficial in treating other tumors. Such a determination can be made by a person skilled in the art, in accordance with methods known in the art and described in the Examples provided below. Some preferred combinations, containing at least one triterpene glycoside compound in the ethyl acetate extract of black cohosh, and at least one additional chemopreventive or chemotherapeutic agent, may be formulated such that the amount of the triterpene glycoside is selected synergistically to enhance the effect of the chemopreventive or chemotherapeutic agents, while alleviating unwanted side effects attributable to such agents. Exemplary combinations comprising the ethyl acetate extract of black cohosh, and at least one additional chemopreventive or chemotherapeutic agent, are described above. In a preferred embodiment of the present invention, the combination comprises actein (e.g., about 0.5 μg/ml to about 5.0 μg/ml) and paclitaxel (e.g., about 0.5 nM to about 5.0 nM).

In the combination of anti-neoplastic agents of the present invention, the ethyl acetate extract of black cohosh, or the actein composition, and the one or more additional chemopreventive or chemotherapeutic agents, may be combined in a single formulation, such that the extract is in physical association with the agent. This single, combined formulation may consist of a liquid mixture, containing amounts of both the extract and the agent, which may be injected into a subject, or an oral formulation, containing amounts of both the extract and the agent, which may be orally administered to a subject.

Alternatively, in the combination of the present invention, a separate, individual formulation of the extract may be combined with a separate, individual formulation of the agent. For example, an amount of the extract may be packaged in a vial or unit dose, and an amount of the agent may be packaged in a separate vial or unit dose. A combination of the extract and the agent then may be produced by mixing the contents of the separate vials or unit doses in vitro. Additionally, a synergistic combination of the extract and the agent may be produced in vivo by co-administering to a subject the contents of the separate vials or unit doses, according to the methods described above. Accordingly, the combination of the present invention is not limited to a combination in which amounts of the extract and the agent are in physical association with one another in a single formulation.

It is also within the confines of the present invention for the ethyl acetate extract of black cohosh, or the actein composition, and the one or more additional chemopreventive or chemotherapeutic agents, to be co-administered in combination with radiation therapy or an anti-angiogenic compound (either natural or synthetic). Examples of anti-angiogenic compounds with which the anti-neoplastic agents may be combined include, without limitation, angiostatin, thalidomide, and thrombospondin.

The combination of anti-neoplastic agents of the present invention comprises an effective anti-neoplastic amount of the ethyl acetate extract of black cohosh and an effective anti-neoplastic amount of the one or more additional chemopreventive or chemotherapeutic agents. As used herein, an "effective anti-neoplastic amount" of the extract or the agent is an amount of the extract or the agent that is effective to ameliorate or minimize the clinical impairment or symptoms of neoplasia in a subject, in either a single or multiple dose.

The present invention is described in the following Examples, which are set forth to aid in the understanding of the invention, and should not be construed to limit in any way the scope of the invention as defined in the claims which follow thereafter.

EXAMPLES

Example 1

Chemicals and Reagents

Polyamide resin SC6<0.07 mm was purchased from Alltech Associates, Inc. (Deerfield, Ill.). $RP_{18}CC$ silica gel (40 μM) was obtained from J. T. Baker (Phillipsburg, N.J.), and the $RP_{18}F_{254}$ plate (1-mm layer thickness) was obtained from EM Science (Darmstadt, Germany). Actein, 27-deoxyactein (23-epi-26-deoxyactein) (Zheng et al., CimiPure (*Cimicifuga racemosa*): a standardized black cohosh extract with novel triterpene glycoside for menopausal women. In *Phytochem. Phytopharm.*, Shahidi and Ho, eds. (Champaign, Ill.: AOCS Press, 2000) pp. 360-70), cimifugoside, and cimiracemoside A were obtained from ChromaDex (Laguna Hills, Calif.), and 27-deoxyactein was also obtained from Herbstandard (Chesterfield, Mo.). Tamoxifen, 5-fluorouracil (5-FU), doxorubicin, cisplatin, and paclitaxel were purchased from Sigma (St. Louis, Mo.). Herceptin was obtained from Genentech (CA). Cimigenol and cimigenol glycoside were obtained from Dr. W C Ye (Department of Phytochemistry, China Pharmaceutical University, Nanjing 210009, China).

Black cohosh extracts and purified components were dissolved in dimethylsulfoxide (DMSO) (Sigma Chemical Co.). Water ($H_2O$) was distilled and deionized. All solvents and reagents were reagent grade.

Example 2

Plant Material

Black cohosh roots and rhizomes (GFP) were obtained from PureWorld Botanicals (South Hackensack, N.J.; lot number 9-2677).

Example 3

Separation of the Ethyl Acetate Extract

As shown in FIG. 1, black cohosh roots and rhizomes were extracted with 80% methanol (MeOH)/$H_2O$, and partitioned with n-hexane. Two layers were obtained: a water layer and an n-hexane layer. N-hexane was used to extract the non-polar phytochemicals, respectively, with yields of 0.05% hexane, 0.73% ethyl acetate, and 1.69% water. The water layer was partitioned with ethyl acetate, and two fractions were obtained: a water layer and an ethyl acetate layer. Ethyl acetate was used to extract the mid-polar and polar phytochemicals. The ethyl acetate layer was dried and evaporated to yield an ethyl acetate extract. The triterpene glycosides and cinnamic acid esters were separated from the ethyl acetate extract by polyamide chromatography (Kruse et al., Fukic and piscidic acid esters from the rhizome of *Cimicifuga racemosa* and the in vitro estrogenic activity of fukinolic acid. *Planta. Med.*, 65:763-64, 1999).

Example 4

Cell Cultures

MDA-MB-453 human breast cancer cells (HER2 overexpressing, ER negative), MCF7 cells (ER positive, HER2 low), MDA-MB-231 cells (ER negative, HER2 low), MCF10F cells (normal mammary epithelial cells), and SW480 colon cancer cells were obtained from ATCC (Manassas, Va.). BT474 clone Sc-1 cells (ER positive, Her2 overexpressing) were the kind gift of Dr. S. Friedman (Incyte Pharmaceuticals). Cells were grown in Dulbecco's Modified Eagle medium (DMEM) (Gibco BRL Life Technologies, Inc., Rockville, Md.) containing 10% (v/v) fetal bovine serum (FBS) (Gibco BRL), at 37° C. and 5% $CO_2$. The medium was supplemented with bovine insulin (0.01 mg/ml) for the growth of BT474 cells.

Example 5

Cell-Growth Assays

Cell cultures were treated with increasing concentrations of extracts and/or purified compounds for increasing times and cytoxicity (for SW480 cells) measured using the MTT {3-(4,5-dimethyl-2-thiazol)-2,5-diphenyl-2H tetrazolilum bromide} (Dojindo, Tokyo, Japan) method (Luo et al., PM-3, a benzo-g-pyran derivative isolated from propolis, inhibits growth of MCF-7 human breast cancer cells. Anticancer Res 21: 1665-1672, 2001) and inhibition of cell proliferation by performing cell counts using a Coulter Counter (Lim et al., 1999, supra). For the cell count assay, breast cancer cells were seeded, in triplicate, at $2\times10^4$ cells per well, in 24- or 96-well plates. Two or 3 days later, the medium was replaced with fresh medium—with or without black cohosh extracts or purified compounds—and the number of attached viable cells was counted at increasing times (or, to determine $IC_{50}$ values, at 48 or 96 h), using a Coulter Counter, model $Z_F$ (Coulter Electronics Inc., Hialeah, Fla.) (Lim et al., Sulindac derivatives inhibit growth and induce apoptosis in human prostate cancer cell lines. *Biochem. Pharmacol.*, 58:1097-107, 1999).

For the MTT assay, cells were seeded at $3\times10^3$ cells per well in 96-well plates; 24 hours later the medium was replaced with fresh medium containing black cohosh extracts or components and assayed with MTT reagents at 48 hours.

To determine the combination index (CI) for potential combination therapies, the inventors treated the breast cancer cells with all combinations of 3 concentrations of the black cohosh component and 3 concentrations of the chemotherapy agent, using a solvent control. Surviving cells were counted using the Coulter Counter (Masuda et al., Effects of epigallocatechin-3-gallate on growth, epidermal growth factor receptor signaling pathways, gene expression, and chemosensitivity in human head and neck squamous cell carcinoma cell lines. *Clinical Cancer Research*, 7:4220-29, 2001). Data that were obtained were analyzed for possible synergistic effects using previously-described methods (e.g., the median-effect plot method of Chou and Talalay (Quantitative analysis of dose-effect relationships: the combined effects of multiple drugs or enzyme inhibitors. *Adv. Enzyme Regul.*, 22:27-55, 1984)). The CIs were calculated using the index-isobologram method (Soriano et al., Synergistic effects of new chemopreventive agents and conventional cytotoxic agents against human lung cancer cell lines. *Cancer Res.*, 59:61, 78-84, 1999) based on the median-effect principle of Chou and Talalay, 1984, supra.

Example 6

Statistical Analysis

The inventors were interested in determining the effects of combinations of actein and paclitaxel concentrations on MDA-MB-453 cells. In calculating statistical significance, a Two-Way Analysis of Variance (ANOVA) was performed to test whether the effects of paclitaxel and actein concentrations were independent, or were related, or "interacted" with each other (alpha=0.05; significant difference=$p<0.05$; very significant difference=$p<0.01$). If the F-test showed that the interaction was significant, the Least Significant Difference method (LSD) was then used for multiple comparisons, to clarify the significance between the different combinations of paclitaxel and actein concentrations.

Example 7

Cell-Cycle Analysis

To obtain exponential cultures of breast cancer cells, $3\times10^5$ cells were plated onto 10-cm dishes, and grown for 2-3 days; the medium was then replaced with fresh medium containing black cohosh extracts or purified components alone and in combination with chemotherapy agents. Synchrony: To synchronize the cells, $3\times10^5$ cells were plated onto 10 cm dishes and grown for 2 days in DMEM supplemented with 10% fetal bovine serum. The medium was then replaced with DMEM containing 0.25% FBS (Imoto et al., 1997) and black cohosh extracts or purified components.

After incubation for 1-3 days, the supernatant was collected, and the cells were trypsinized, collected, and washed with phosphate buffered saline (PBS) containing 5% FBS. Cell pellets were re-suspended in 1 ml of PBS plus 5% FBS. Thereafter, 5 ml of 70% ethanol were added drop-wise, while vortexing the tube, and the mixture was stored at 4° C. Cells were centrifuged, washed with PBS plus 5% FBS, and re-suspended in 400 µl of propidium iodide (0.1 mg/ml) (Sigma Chemical Co.). 400 µl (2 mg/ml) of RNase (Sigma Chemical Co.) were added, and the cells were incubated in the dark at room temperature for 30 min. The suspension was filtered through a 41-µM spectra/mesh filter (Spectrum Medical Industries, CA), and analyzed with a FACScalibur instrument (Becton Dickinson, Franklin Lakes, N.J.) equipped with Cell Quest software (Becton Dickinson). The percentage of cells in different cell-cycle phases was then calculated (Lim et al., Sulindac derivatives inhibit growth and induce apoptosis in human prostate cancer cell lines. *Biochem. Pharmacol.*, 58:1097-107, 1999; Luo et al., PM-3, a benzo-g-pyran derivative isolated from propolis, inhibits growth of MCF7 human breast cancer cells. *Anticancer Research*, 21:1665-72, 2001; Soh et al., Cyclic GMP mediates apoptosis induced by sulindac derivatives via activation of c-Jun NH2-terminal kinase 1. *Clin. Cancer Res.*, 10:4136-41, 2000).

Example 8

Western-Blot Analysis

Cells were treated for increasing times with approximately the $IC_{50}$ concentration, or twice the $IC_{50}$ concentration, of actein. The cells were harvested, washed with PBS, and sonicated in extraction buffer according to the procedure of Han et al. (Han et al., Stable overexpression of cyclin D1 in a human mammary epithelial cell line prolongs the S-phase and inhibits growth. *Oncogene*, 10:953-61, 1995). The lysates were subjected to electrophoresis on a 10% or 12.5% SDS-polyacrylamide gel, and then transferred to a polyvinylidene difluoride (PVDF) membrane. The membrane was blocked with milk protein, and incubated with a solution containing the primary antibody against the following: cyclin D1 (Upstate Biotechnology, Lake Placid, N.Y.), $p21^{cip1}$ (Oncogene Research Products, Darmstadt, Germany), ppRb (ser 780, Medical and Biological Laboratories, Nagoya, Japan), cdk4 (Upstate Biotechnology, Lake Placid, N.Y.), EGFR (clone-74, Transduction Laboratories, Lexington, Ky.), p-EGFR (phospho (Y1173)-EGFR) (Cell Signaling, Beverly, Mass.), actin (Sigma, St. Louis, Mo.), Her-2/neu (Cell Signaling, Beverly, Mass.), or phospho-(Y1248)-Her-2/neu (Cell Signaling, Beverly, Mass.) ), IκB (Sant Cruz Biotechnolgy, Santa Cruz, Calif.), IκκB (Sigma, St. Louis, Mo.) and PPARγ (Santa Cruz biotechnology, Santa Cruz, Calif.) (Masuda et al., Epigallocatechin-3-gallate inhibits activation of HER-2/neu and downstream signaling pathways in human head and neck and breast carcinoma cells. *Clin. Cancer Res.*, 9: 3486-91, 2003). The membrane was washed, and incubated with horseradish peroxidase conjugated secondary antibody.

Protein bands were visualized with the ECL-enhanced chemiluminescence system, according to the manufacturer's directions (Amersham Pharmacia Biotech) (Sgambato et al., Overexpression of p27 (Kip1) inhibits the growth of both normal and transformed human mammary epithelial cells. *Cancer Research*, 58:3448-54, 1998). The staining intensities of the visualized blots were quantified using NIH image software. For each protein, the relative band intensities were determined by comparing treated samples with untreated controls. These values were then normalized, using β-actin as an internal control.

Example 9

Thin-Layer Chromatography Analysis

Extracts were tested for triterpene glycosides and cinnamic acid esters using silica gel 60 $F_{254}$ plates (0.25-mm layer thickness) and $RP_{18}F_{254}$ plates (1-mm layer thickness) from EM Science (Darmstadt, Germany). The solvent system for the silica gel thin-layer chromatography (TLC) was chloroform-MeOH (9:1); the solvent system for the $RP_{18}$ plates was MeOH-H2O (9:1). After development, the compounds were visualized under UV, and visualized by spraying with vanillin in 10% (v/v) $H_2SO_4$ in ethanol (EtOH).

Example 10

Polyamide Chromatography

Polyamide SC6 resin (1.5 gm), pre-conditioned with MeOH (15 min) and $H_2O$ (10 min), was packed under pressure in a 12-ml syringe (approximately 3.3 cm in height, with a column volume of 4.5 ml); the syringe was then rinsed with water. The black cohosh ethyl acetate extract (100 mg) was dissolved in 1 ml of $H_2O$/MeOH (1:1), and adsorbed to the polyamide column for 20 min before elution. The column was then eluted sequentially, twice, with 6 ml of $H_2O$/MeOH (50:50), $H_2O$/MeOH (75:25), MeOH, EtOH, and EtOH+ 0.1% TFA, to yield 10 fractions (Kruse et al., Fukic and piscidic acid esters from the rhizome of *Cimicifuga racemosa* and the in vitro estrogenic activity of fukinolic acid. *Planta. Med.*, 65:763-64, 1999).

Example 11

Cyclin D1 Reporter Assay

The cyclin D1 promoter luciferase reporter plasmid, 1745CD1LUC, was prepared by Dr. R. Pestell (Albert Einstein Cancer Center, New York, N.Y.). The method used for transient transfection reporter assays was previously described (Soh et al., Novel roles of specific isoforms of protein kinase C in activation of the c-fos serum response element. *Molecular and Cellular Biology*, 19:1313-24, 1999). Using lipofectin, triplicate samples of MDA-MB-453 breast cancer cells ($1\times10^5$ cells in 35-mm plates) were co-transfected using DNA of the indicated reporter plasmid (1 μg) and the β-gal plasmid as an internal control (10 μg of the pCMV-b-gal plasmid) in opti-MEM 1 medium (Life Technologies, Inc.). After 24 h, the medium was replaced with serum-free medium containing the indicated concentrations of actein. After 24 h, cells were harvested, and luciferase activity was determined with the luciferase assay system (Promega Corp. Madison, Wis.); β-gal activities were determined with the β-gal enzyme assay system (Promega). Luciferase activities were normalized to β-gal activities, to correct for differences in transfection efficiency.

Example 12

Bioactivity-Guided Fractionation

Open chromatography techniques were used to fractionate the extracts further. The stationary phases used included Diaion HP-20, Sephadex, normal and reversed-phase silica, and polyamide.

1. Alcoholic black cohosh powder extract was redissolved in MeOH/$H_2O$, and evaporated to dryness, leaving the water portion.

2. To partition the phytochemicals according to polarity, the water portion was partitioned sequentially with hexane and n-butanol (n-BuOH). The three resulting fractions—hexane, n-BuOH, and water—were evaporated to dryness, and tested for their effects on the growth of MCF7 breast cancer cells. The n-BuOH extract showed high activity (FIG. 11).

3. The n-BuOH extract was further separated using Diaion HP-20 as a stationary phase, and eluting sequentially with MeOH/$H_2O$ (1:1), MeOH, and acetone. By thin-layer chromatography, the MeOH/$H_2O$ (1:1) contained mostly UV-absorbing compounds (aromatic acid derivatives), while the MeOH contained mostly triterpenoids (FIG. 11).

Figure 12:
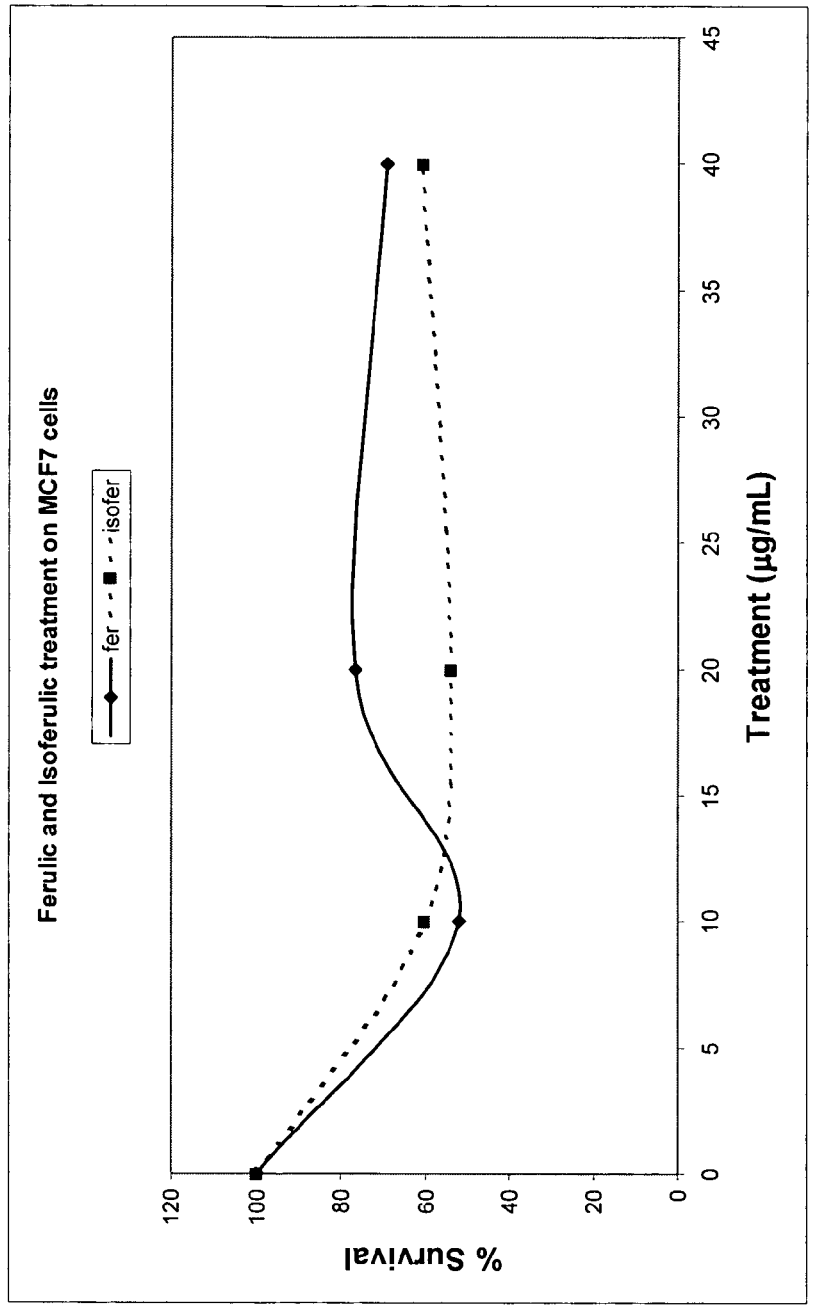
FIG. 12 demonstrates the effects of the components ferulic and isoferulic acid, purified from black cohosh, on cell proliferation in MCF7 cells. MCF7 cells were exposed to increasing concentrations of the indicated purified components for 96 hrs, and the number of viable cells was determined using a Coulter Counter.

4. Further separation of the MeOH/$H_2O$ fraction, over silica gel, $RP_{18}$, and polyamide columns, yielded isoferulic acid, ferulic acid, and caffeic acid. Preliminary experiments indicated that isoferulic, the more potent, and ferulic acids were active in suppressing the growth of MCF7 human breast cancer cells (FIG. 12).

Summarized below are results obtained by the inventors in connection with the experiments described in Examples 1-12:

Effects of Extracts of Black Cohosh on the Growth of Human Breast Cancer Cells

Black cohosh roots and rhizomes were extracted with MeOH/$H_2O$, and fractionated by solvent-solvent partitioning to yield three fractions: hexane, ethyl acetate (EtOAc), and $H_2O$ (FIG. 1). These fractions were assayed for growth inhibition on human breast cancer cell lines. By TLC, it was determined that triterpene glycosides are present at the highest level in the EtOAc extract; low levels were detected in the hexane and water extracts.

The effects of increasing amounts of the three black cohosh fractions on the growth of the (ER+) human breast cancer cell line, MCF7, were determined after exposure of the cells for 96 h. The results, expressed as $IC_{50}$ values (i.e., the concentration that causes approximately 50% inhibition of growth), are set forth in Table 1. The results indicate that the EtOAc extract was the most active fraction.

The inventors tested the effects of crude extracts, methanol and ethanol, as well as ethanol extracts provided by Pure World, native and plus expedient: the $IC_{50}$ values for these extracts after 96 hours of treatment of MDA-MB-453 cells were: methanol: 100 µg/ml; ethanol: >200 µg/ml; PW native 175 µg/ml: and PW expedient: 195 µg/ml.

To partition the phytochemicals according to polarity, the water portion was also partitioned sequentially with hexane and n-butanol (n-BuOH). The n-BuOH fraction was tested for its effect on the growth of MDA-MB-453 breast cancer cells. The IC50 value after 96 hours of treatment was: 40 µg/ml.

The inventors also examined the effects of the EtOAc fraction of black cohosh on SW480 human colon cancer cells. The IC50 values after 48 hours of incubation using the MTT assay were: SW480: 42 µg/ml; MCF7: 38 µg/ml (Luo et al., PM-3, a benzo-g-pyran derivative isolated from propolis, inhibits growth of MCF-7 human breast cancer cells. *Anticancer. Res*. 21: 1665-1672, 2001).

TABLE 1

Effects of black cohosh extracts on MCF7 cells.

|  | $IC_{50}$ Values (µg/ml) |
|---|---|
| Black Cohosh Extracts |  |
| H₂O extract | 150 |
| ethyl acetate extract | 18 |
| hexane extract | 28 |
| Purified Components |  |
| Actein | 14 (21 µM) |
| 23-epi-26-deoxyactein | 21 (32 µM) |
| Cimifugoside | 22 (36 µM) |
| cimiracemoside A | 41 (61 µM) |

Figure 2A:
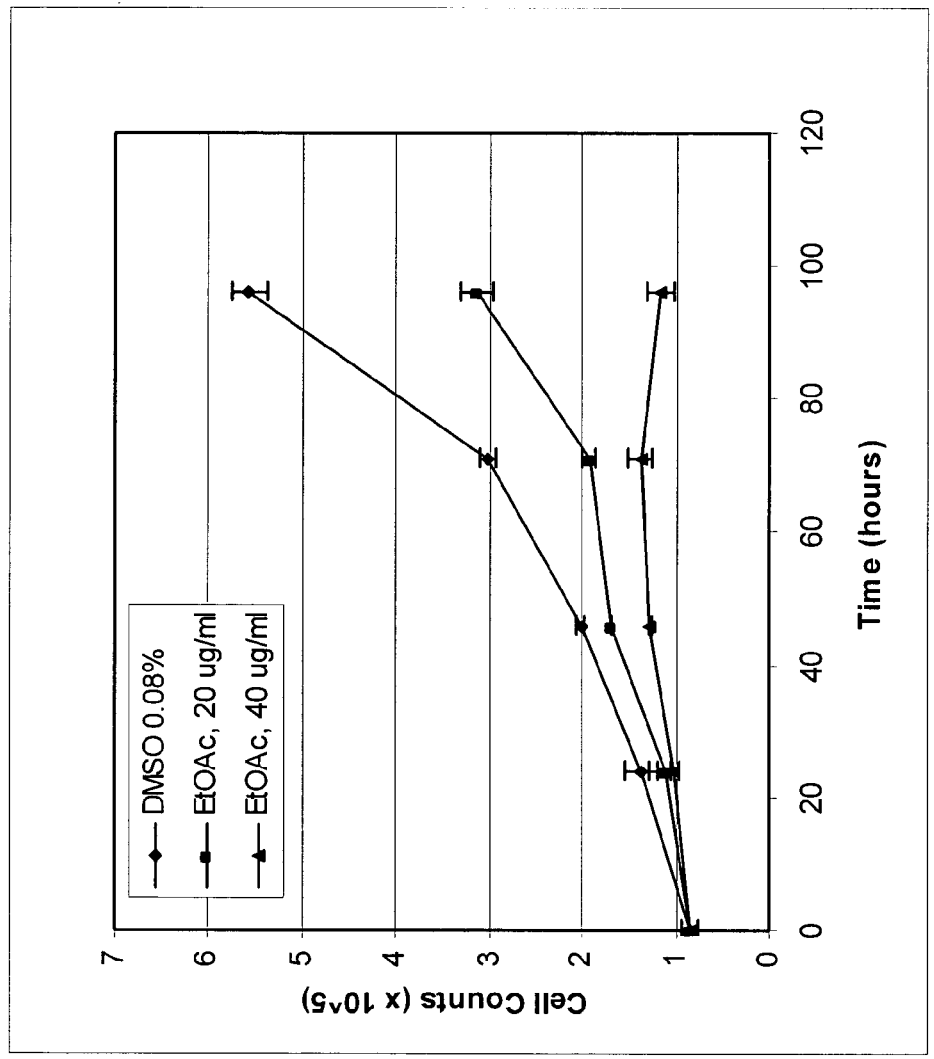
FIGS. 2A and 2B illustrate the effect of black cohosh extracts on the growth of MCF7 cells.

The effects of two concentrations of the EtOAc fraction on the growth of MCF7 cells were examined at increasing times. Exposure to 20 µg/ml of the EtOAc fraction led to partial inhibition of cell proliferation as early as 24 h after addition; 40 µg/ml resulted in complete inhibition and cell death after 72 h (FIG. 2A), while 60 µg/ml resulted in cell death at 24 h.

Two major signaling pathways in breast cancer cells are the ER-mediated signaling pathway (exemplified in the estrogen-dependent human breast cancer cell line, MCF7) and the HER2-mediated signaling pathway (exemplified in the estrogen-independent human breast cancer cell line, MDA-MB-453, which overexpresses HER2 (erb2, c-neu), a membrane-associated tyrosine kinase receptor (p185 HER2)). Clinical studies indicate that a reciprocal relationship often occurs in the expression of the two pathways in primary human breast cancers (Tsutsui et al., Prognostic value of c-erbB2 expression in breast cancer. *J. Surg. Oncol*., 79:216-33, 2002). It was important, therefore, for the inventors to determine if black cohosh extracts have different effects on the two cell types. Accordingly, the following three breast cancer cell lines were tested: MCF7 (ER positive, HER2 low), MDA-MB-231 (ER negative, HER2 low), and MDA-MB-453 (HER2 overexpressing, ER negative).

Treatment with the EtOAc fraction for 48 h inhibited the growth of all three cell lines, with $IC_{50}$ values in the range of 20-40 µg/ml (Table 2). The Her2 overexpressing cells were the most sensitive. It is of interest that the normal human mammary epithelial cell line, MCF10F, was considerably less sensitive, with an $IC_{50}$ value of 85 µg/ml.

TABLE 2

Effects of black cohosh extracts on breast cancer cells.

| Cells | Receptors Expressed | $IC_{50}$ (µg/ml) |
|---|---|---|
| MDA-MB-453 | ER−/HER2+ | 18 |
| MCF7 | ER+/HER2− | 35 |
| MDA-MB-231 | ER+/HER2− | 39 |
| MCF10F | Normal Mammary Epithelial Cells (ER−) | 85 |

Observed over a 48-h period, the approximate doubling times for the malignant cells were 36 h for MDA-MB-453, 32 h for MCF7, and 30 h for MDA-MB-231; the approximate doubling time for the non-malignant MCF10F cells was 48 h. It is possible that the greater sensitivity of the malignant cells may reflect, in part, the difference in growth rates. The $IC_{50}$ values were less when the cells were treated for 96 h: 18 µg/ml for MCF7 cells, 10 µg/ml for MDA-MB-453 cells, and 46 µg/ml for MCF10F cells. Based upon these results, it can be concluded that the EtOAc fraction of black cohosh does not act specifically through the ER or the Her2 receptors.

Characterization of the Active Components in the Ethyl Acetate Extract

As the ethyl acetate extract of black cohosh contains many components, it was important for the inventors to identify the specific active compounds and their modes of action.

To separate the triterpene glycosides from the aromatic acids and esters, the ethyl acetate extract was fractionated on a polyamide SC6 column (Kruse et al., Fukic and piscidic acid esters from the rhizome of *Cimicifuga racemosa* and the in vitro estrogenic activity of fukinolic acid. *Planta. Med*., 65:763-64, 1999). The first four fractions (water/methanol—50:50; 75:25), which are enriched for triterpene glycosides, suppressed the growth of MCF7 cells. Incubation with fraction 1 (5.7 µg/ml) resulted in 25% cell death; incubation with fraction 2 (23 µg/ml) resulted in 67% cell death; and incubation with fraction 3 (30 µg/ml) resulted in 73% cell death. In view of these results, it appears that the triterpene glycosides are among the active components in the ethyl acetate extract.

Figure 2B:
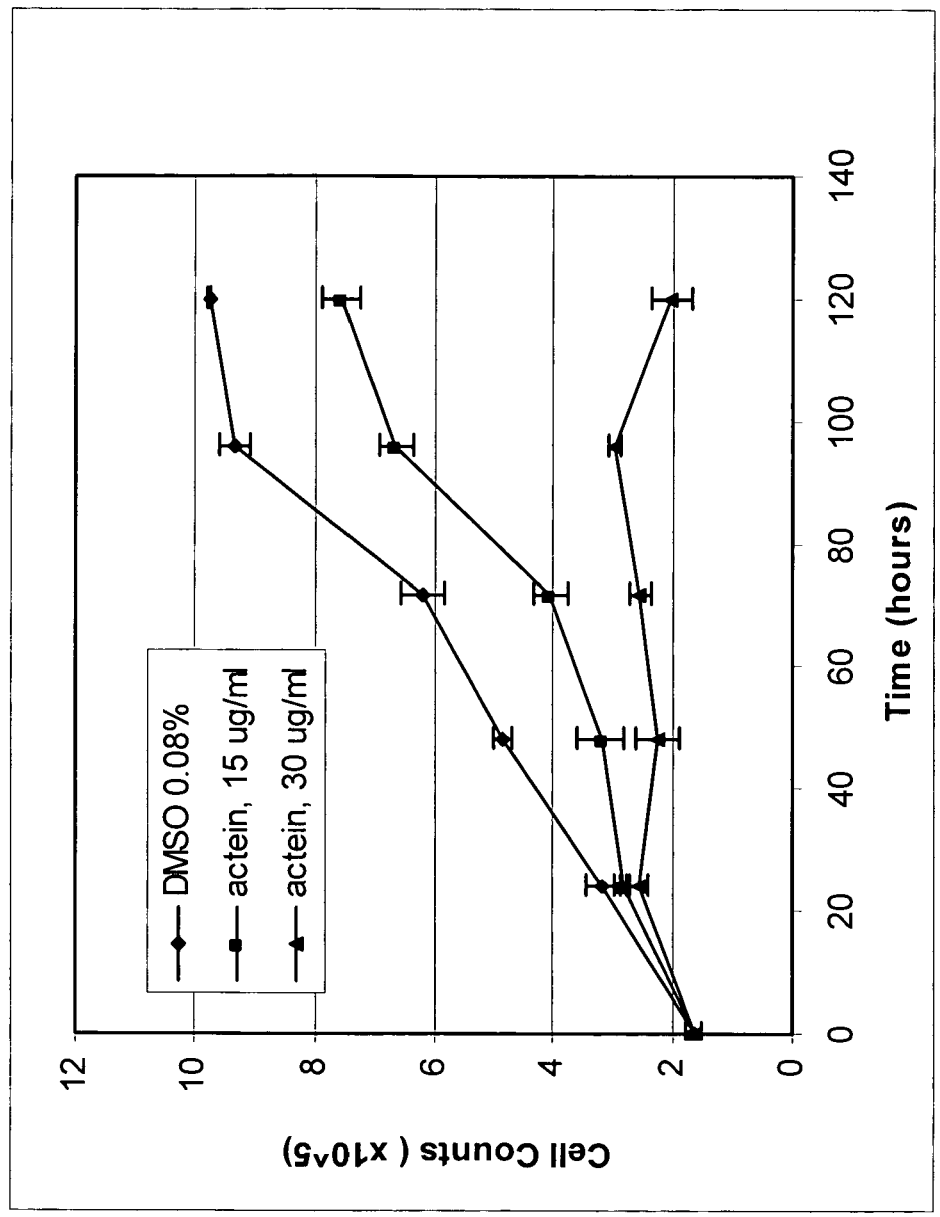
Figure 3:
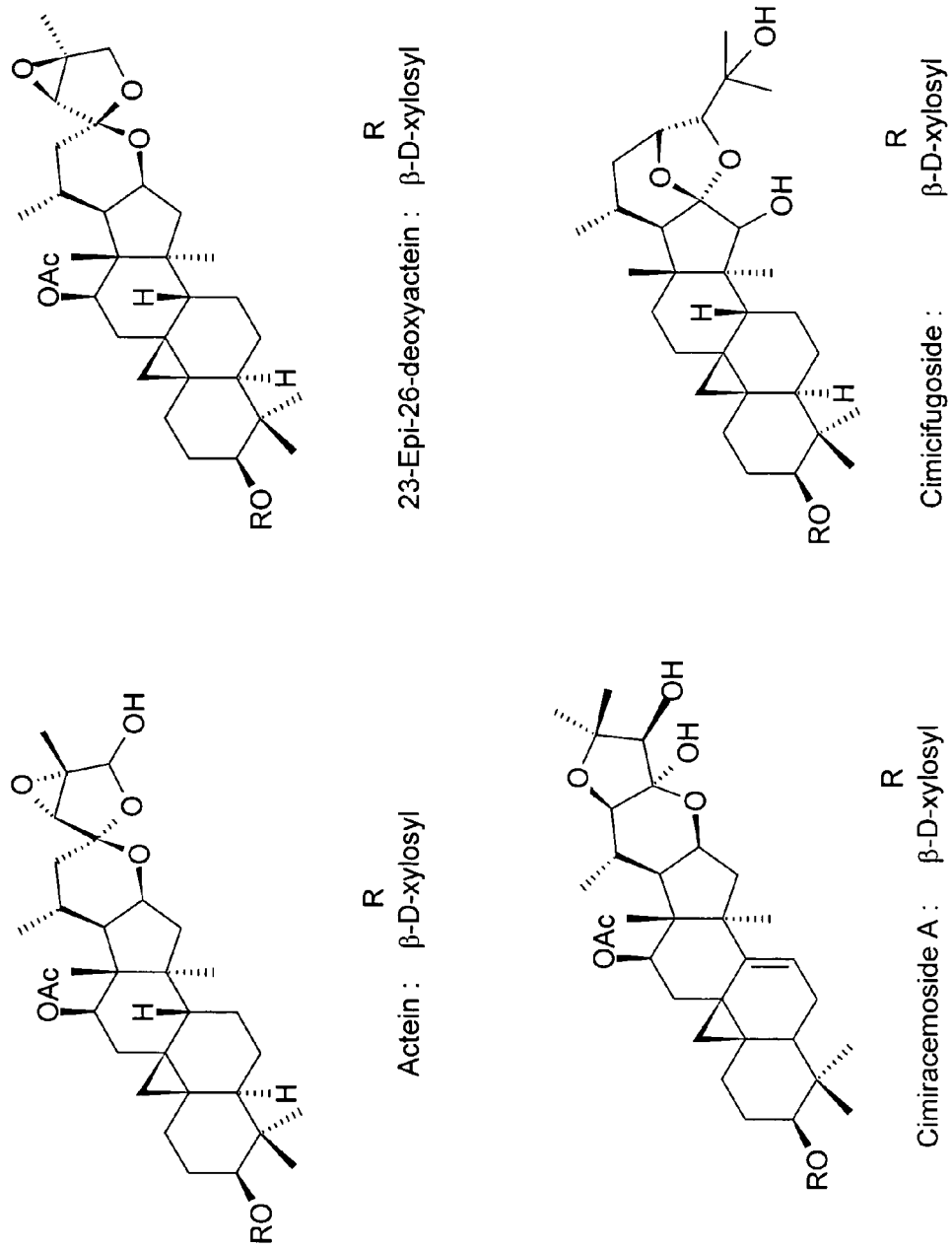
FIG. 3 shows the structures of the triterpene glycoside compounds of the invention.

Effects of Triterpene Glycoside Fraction and Pure Components on Cell Proliferation To ascertain the nature of the triterpene glycosides of black cohosh, the purified triterpene glycosides (set forth in FIG. 3) were tested for growth inhibition on MCF7 cells (FIG. 2B and Table 1). Actein, which has an hydroxyl group on the C-26 position of 23-epi-26-deoxyactein (Chen et al., Isolation, structure elucidation, and absolute configuration of 26-deoxyactein from *Cimicifuga racemosa* and clarification of nomenclature associated with 27-deoxyactein. *J. Nat. Prod*., 65:601-05, 2000)), had an $IC_{50}$ of 21 µM; it was approximately 1.5-fold more potent than 23-epi-26-deoxyactein or cimifugoside, and approximately 3 times more potent than cimiracemoside A, in inhibiting the growth of MCF7 cells (Table 1). The substitution of an hydroxyl on the aglycone moiety can significantly alter this inhibitory activity.

The effects of two concentrations of actein on the proliferation of MCF7 cells were examined at increasing times. Treatment with actein (15 µg/ml) resulted in partial inhibition of growth, within 24 h after addition of the compound, while treatment with actein at 30 μg/ml resulted in complete inhibition of growth (FIG. 2B). In additional studies, it was found that MCF7 cells were approximately three times more sensitive to growth inhibition by actein than the MCF10F normal mammary epithelial cells; the respective $IC_{50}$ values were 14 μ/ml vs. 42 μg/ml, when measured at 96 h of exposure. The mean of the MCF7 cells that were alive (38.0%±3.0) after 96 h of treatment with actein (20 μg/ml) was significantly less than the mean of the MCF10F cells that were alive (63.8%±1.4) after 96 h of treatment with actein (20 μg/ml) ($p<0.01$). As was the case for the EtOAc fraction, the MDA-MB-453 cells were the most sensitive to treatment with actein—with an $IC_{50}$ value of approximately 8 μg/ml at 96 h.

Figure 4:
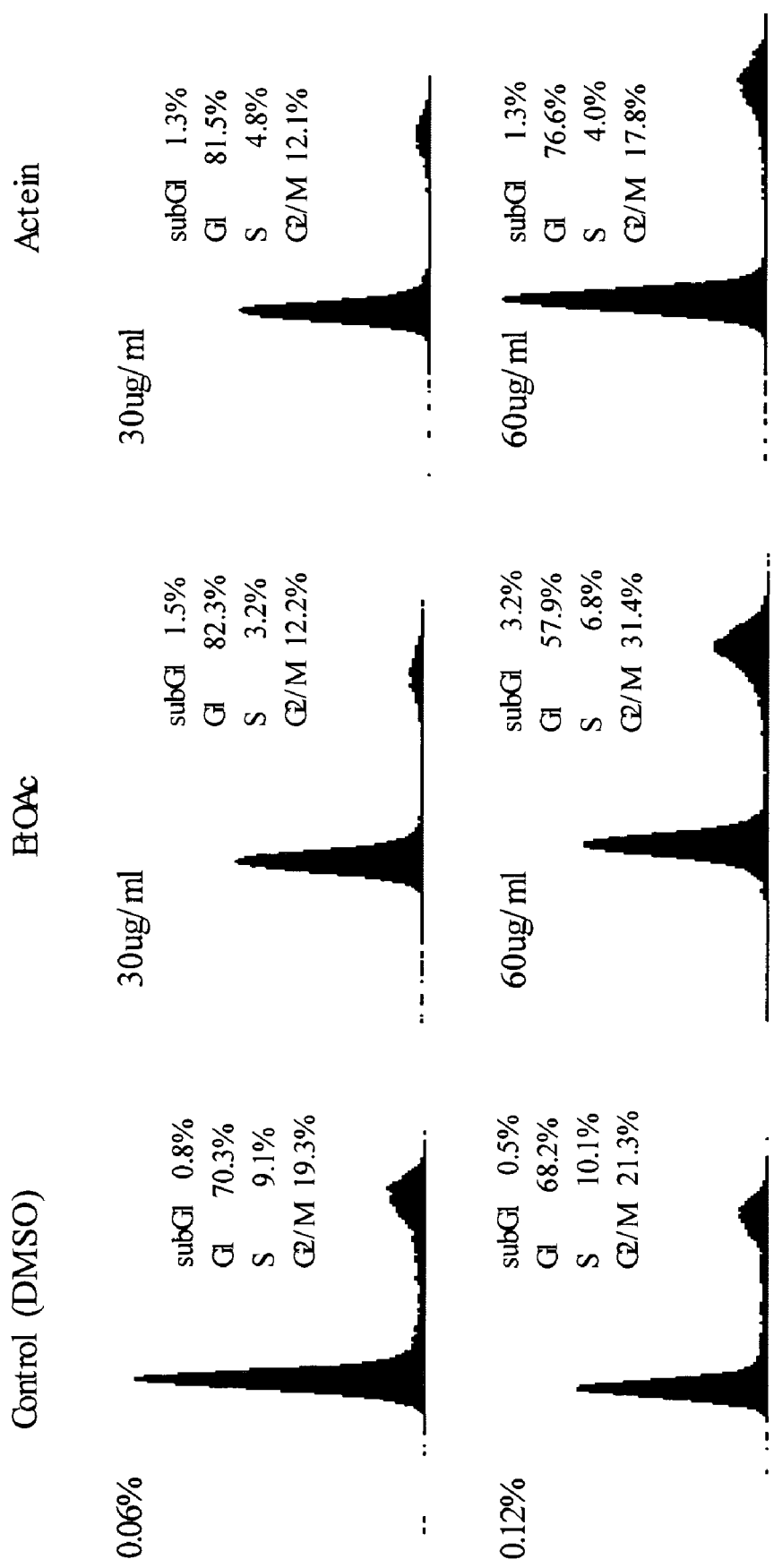
FIG. 4 depicts the effect of actein and the effect of the ethyl acetate fraction of black cohosh on MCF7 cell-cycle distribution at 48 h. MCF7 cells were treated with 0, 30, and 60 µg/ml of the ethyl acetate extract, or actein, and then analyzed at 48 h by DNA flow cytometry. The values indicate the percentage of cells in the indicated phases of the cell cycle.

Effects of the EtOAc Extract and Purified Components of Black Cohosh on Cell-Cycle Kinetics The ability of an extract or purified compound to affect specific phases of the cell cycle may provide clues to its mechanism of action (Weinstein, I. B., Disorders of cell circuitry during multistage carcinogenesis: the role of homeostasis. *Carcinogenesis*, 5:857-64, 2000). To determine the effects of black cohosh on the cell cycle, MCF7 cells were treated with 30 and 60 μg/ml of the EtOAc fraction of black cohosh, or 30 and 60 μg/ml of actein, for 48 h. The cells were then stained with propidium iodide, and analyzed by DNA flow cytometry (FIG. 4). After exposure to 30 μg/ml of the EtOAc fraction, there was an increase of cells in G1 (from 70% to 82%) when compared to the DMSO solvent control, and a concomitant decrease of cells in S (9% to 3%) and G2/M (19% to 12%). After treatment with 60 μg/ml of the EtOAc fraction, there was a decrease of cells in G1 (68% to 58%) and an increase of cells in G2/M (21% to 31%).

The above results indicate that the extract contains more than one component, with the more active or abundant component inducing G1 arrest, and the less active component inducing G2/M arrest, and/or that individual components in the extract exert different effects at different concentrations. To distinguish between these possibilities, cells were treated with the purified compound, actein, at 30 and 60 μg/ml. Exposure to actein at 30 μg/ml also resulted in an increase of cells in G1 (70% to 82%) and a decrease of cells in G2/M (19% to 12%). After exposure to 60 μg/ml of actein, there was also an increase of cells in G1 (68% to 77%), and a decrease of cells in G2/M (21% to 18%). Thus, with 60 μg/ml of actein, the inventors did not observe the increase in G2/M cells that was seen with 60 μg/ml of the EtOAc extract (FIG. 4).

Figure 5:
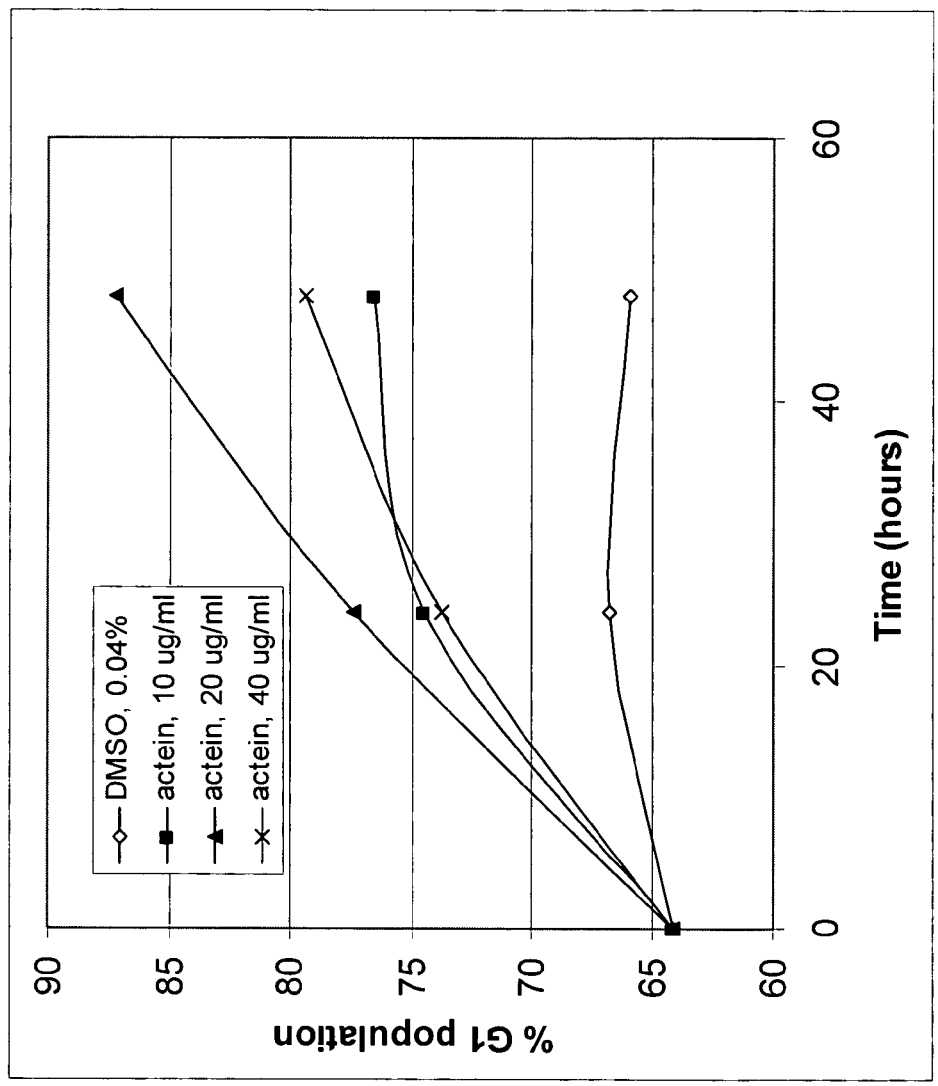
FIG. 5 illustrates the effect of actein on the G1 phase of the cell cycle in MCF7 cells. MCF7 cells were treated with 10 (14.8 µM), 20, or 40 µg/ml actein, and then analyzed at 24 and 48 h by DNA flow cytometry. The values indicate the percentage of cells in the G1 phase of the cell cycle.

To examine in greater detail the effects of actein on cell-cycle progression, MCF7 cells were treated with 0, 10, 20, or 40 μg/ml of actein, and analyzed at 0, 24, and 48 h by DNA flow cytometry. FIG. 5 summarizes the results obtained with respect to the percent of cells in G1. When cells were treated with 10 μg/ml of actein, the percentage of cells in G1 increased from 64% at time zero to 75% at 24 h, and to 77% at 48 h. With 20 μg/ml of actein, the respective values were 64%, 77%, and 87%; with 40 μg/ml of actein, the respective values were 64%, 74%, and 79%. These increases in the G1 population were associated with decreases in both the S and G2/M populations of cells. Indeed, the maximal increase in the G1 population occurred at about 20 μg/ml actein. Therefore, it is possible that, at high concentrations, actein and related compounds affect proteins that regulate later phases in the cell cycle. The triterpene glycoside fraction of black cohosh (polyamide eluate, fraction 3), 23-epi-26-deoxyactein, and cimiracemoside A also induced cell-cycle arrest at G1, when tested at about 40 μg/ml.

Treatment with the EtOAc fraction at 30 μg/ml induced a small amount of apoptosis for 48 h (1.3%); at 60 μg/ml, there was a further increase in apoptosis (3.2%), as determined by the sub G1 fraction (FIG. 4). When the cells were exposed to 20 μg/ml actein for 48 h, approximately 1.4% of the population displayed apoptosis; at 72 h, this value was 3.6%, when assessed by the size of the sub G1 peak.

Effects of Actein on the Expression of Specific Proteins Involved in Cell-Cycle Control and Apoptosis Since actein induces cell-cycle arrest at G1, the inventors examined the effect of actein on proteins which control the progression of the cell cycle. Cyclin D1 was of particular interest, since it plays a critical role in mediating the transition from G1 to S, is overexpressed in approximately 50-60% of primary human breast carcinomas (Joe et al., Cyclin D1 overexpression is more prevalent in non-Caucasian breast cancer. *Anticancer Res.*, 21:3535-39, 2001), and is overexpressed in several human breast cancer cell lines (Han et al., Effects of sulindac and its metabolites on growth and apoptosis in human mammary epithelial and breast carcinoma cell lines. *Breast Cancer Res. Treat.*, 48:195-203, 1998). Therefore, the inventors monitored possible changes in cellular levels of cyclin D1 by Western-blot analysis of extracts obtained from control and actein-treated cells.

Figure 6A:
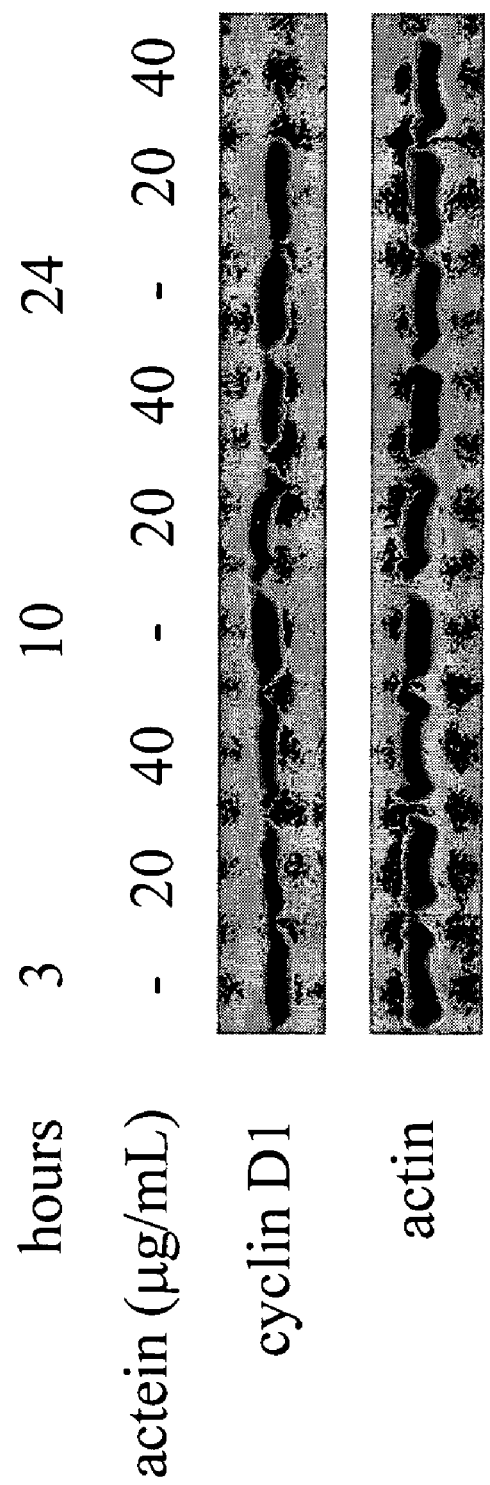
FIGS. 6A-6F show Western-blot analyses of MCF7 cells treated with actein. The cells were treated with 0, 20, or 40 µg/ml actein. 20 µg/ml actein is equivalent to 29.6 µM actein. After 3, 10, and 24 h, extracts were analyzed by Western blotting with antibodies to: cyclin D1 (FIG. 6A); ppRb (FIG. 6B); cdk4 (FIG. 6C); p21$^{cip1}$ (FIG. 6D); EGFR (FIG. 6E); and phospho-EGFR (FIG. 6F). An antibody for β-actin was used as a loading control.

Treatment of MCF7 cells with 40 μg/ml of actein for 3 or 10 h resulted in a partial decrease, and treatment for 24 h caused a marked decrease, in the cellular level of cyclin D1, when compared to comparable time points in the control (untreated) cells. Indeed, after treatment with 40 μg/ml for 24 h, there was almost a complete loss of this protein (FIG. 6A). The MCF10F normal mammary epithelial cells did not express an appreciable level of cyclin D1. Thus, the inventors could not assess the effect of actein on cyclin D1 in these cells.

Figure 6B:
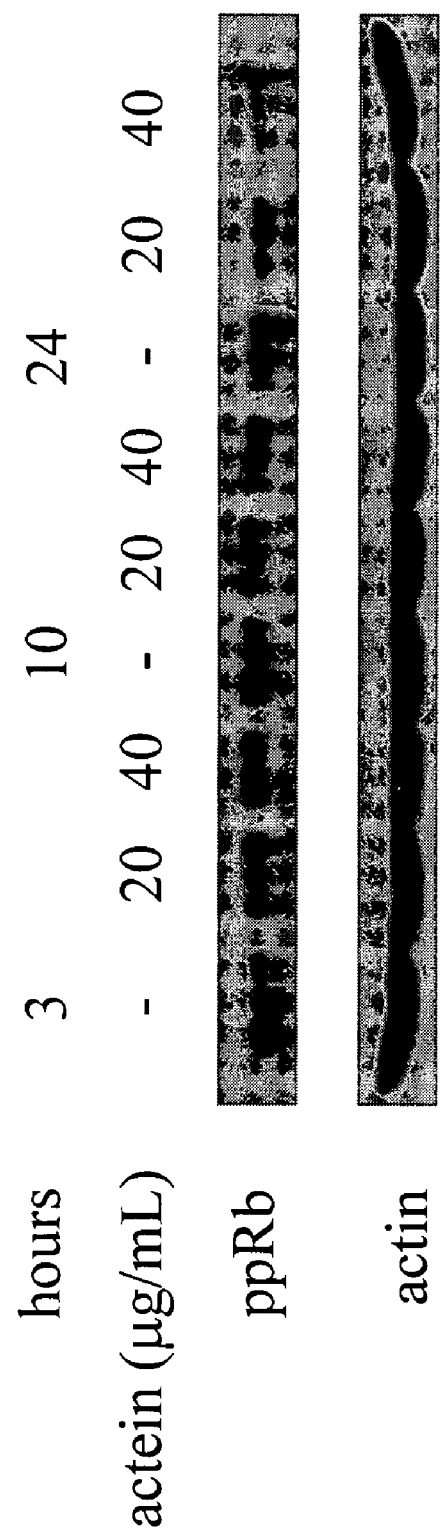
Figure 6C:
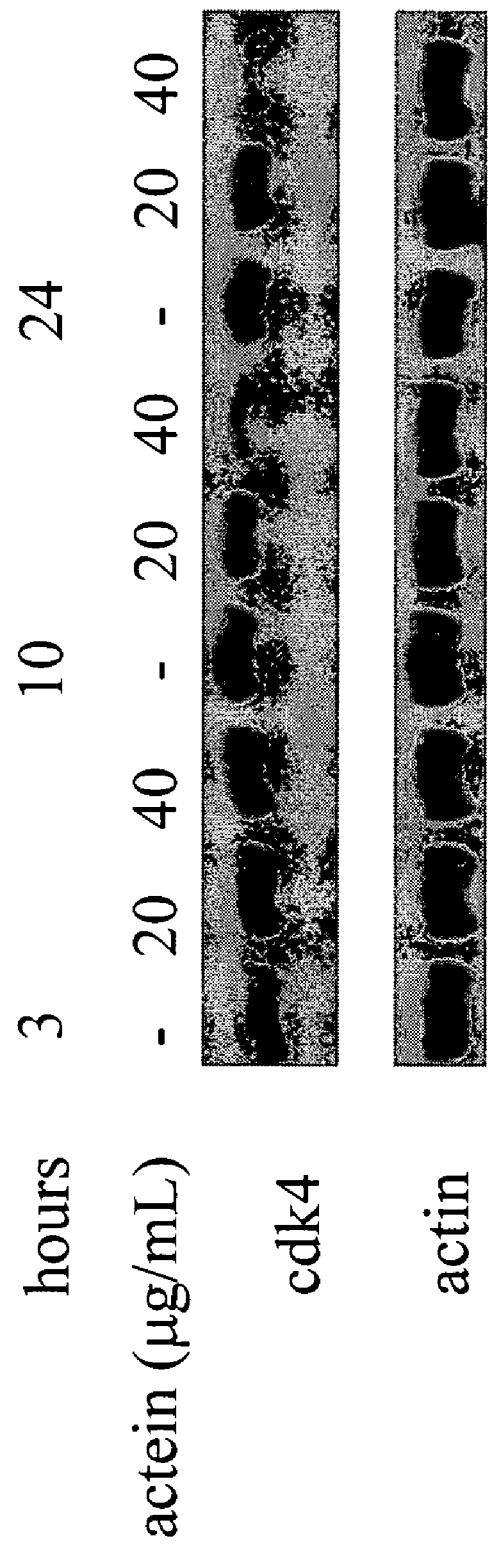

Cyclin D1 binds to and activates the cyclin dependent kinases, cdk4 and cdk6; the resulting complexes phosphorylate and inactivate pRb (retinoblastoma protein), thereby preventing pRb from inhibiting the transcription factor, E2F, and allowing the cells to progress from G1 to S (Weinstein, I. B., Disorders of cell circuitry during multistage carcinogenesis: the role of homeostasis. *Carcinogenesis*, 5:857-64, 2000). The inventors examined the effect of actein on the cellular level of the inactivated, hyperphosphorylated form of Rb (designated ppRb). After treatment with actein, the intensities of the ppRb bands relative to the β-actin bands were: 1.51 (3 h, 20 μg/ml), 1.59 (3 h, 40 μg/ml), 0.61 (10 h, 20 μg/ml), 0.64 (10 h, 40 μg/ml), 0.80 (24 h, 20 μg/ml), and 0.43 (24 h, 40 μg/ml). The inventors found that there was a increase in the level of ppRb at 3 hours and a decrease at 10 hours after treating MCF7 cells with 20 or 40 μg/ml actein; there was a marked decrease at 48 hours after exposure to 40 μg/ml actein (FIG. 6B). The inventors also observed a decrease in the level of cdk4 at 10 hours after treatment with 20 or 40 μg/ml actein and a pronounced decrease at 24 hours after exposure to 40 μg/ml actein (FIG. 6C).

Figure 6D:
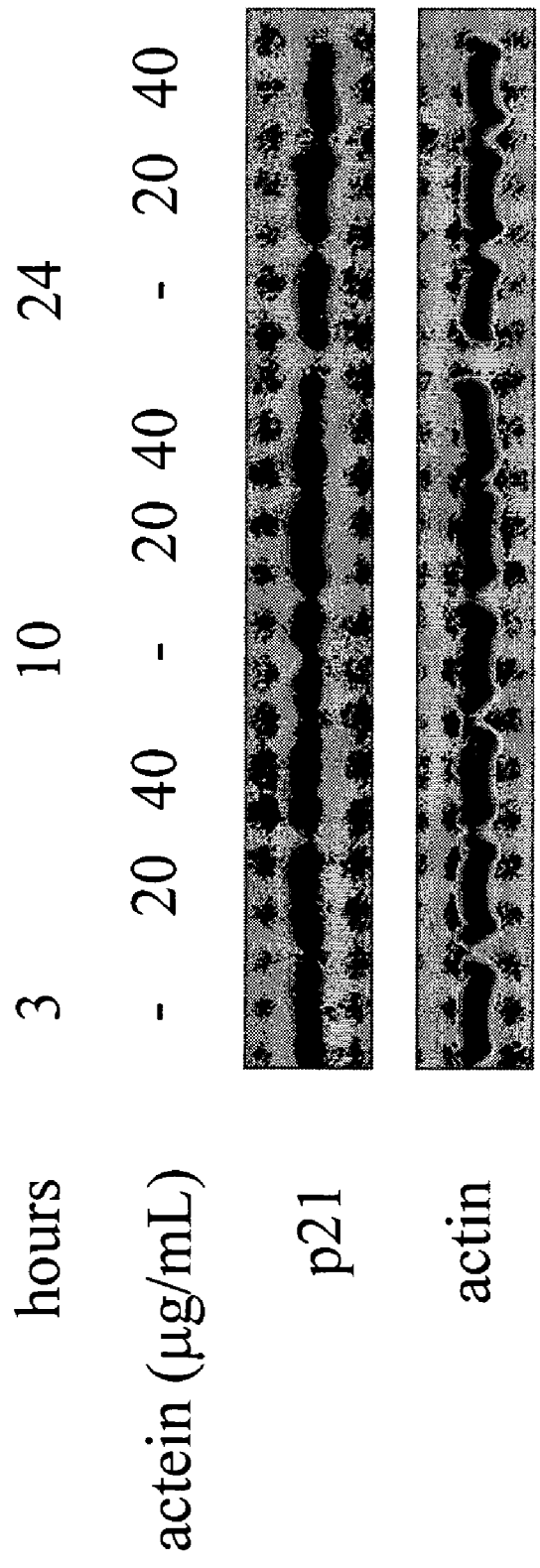

The cdk inhibitory protein $p21^{cip1}$ negatively regulates the activity of the cyclin D1/cdk4 complex. Therefore, the inventors examined the effect of actein on this protein. After exposure to actein, the intensities of the $p21^{cip1}$ bands relative to the β-actin bands were: 1.47 (3 h, 20 μg/ml), 1.17 (3 h, 40 μg/ml), 1.75 (10 h, 20 μg/ml), 1.37 (10 h, 40 μg/ml), 0.94 (24 h, 20 μg/ml), and 0.78 (24 h, 40 μg/ml). Thus treatment of MCF7 cells with 20 or 40 μg/ml of actein induced an increase in $p21^{cip1}$ within 3 hours and this increase persisted at 10 hours. The increase was more pronounced after treatment with 20 μg/ml. However, this increase was not seen with the 20 or 40 μg/ml dose at. 24 hours (FIG. 6D).

In view of the foregoing, the ability of actein to arrest cells in G1 (FIG. 5) may be due to the decreased expression of cyclin D1 and cdk4, and the increased expression of p21$^{cip1}$—both of which result in a decrease in the level of the hyperphosphorylated form of pRb.

Figure 6E:
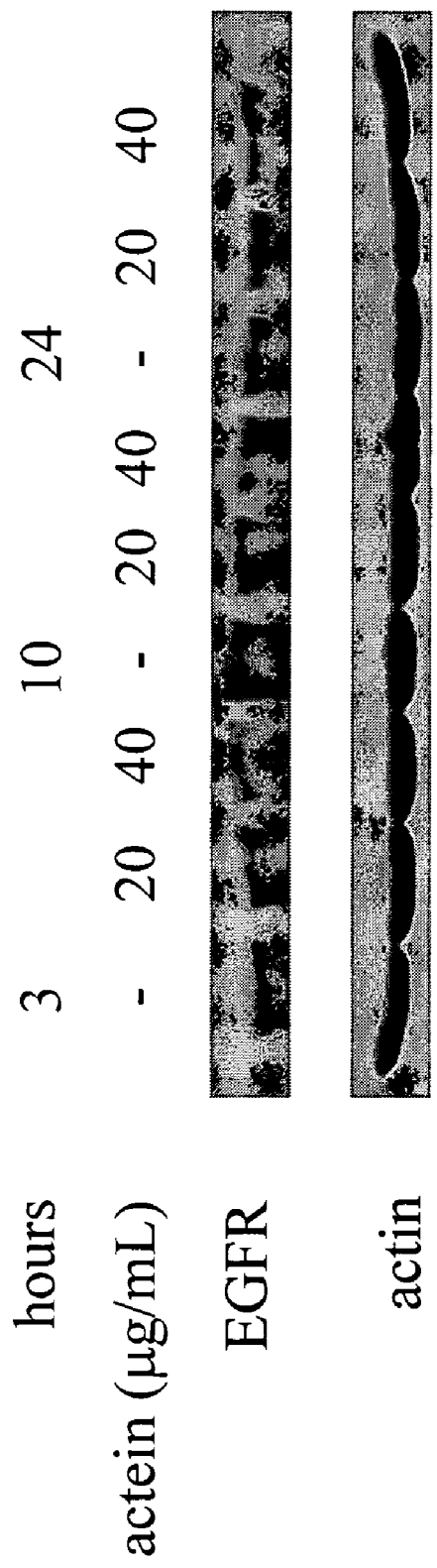
Figure 6F:
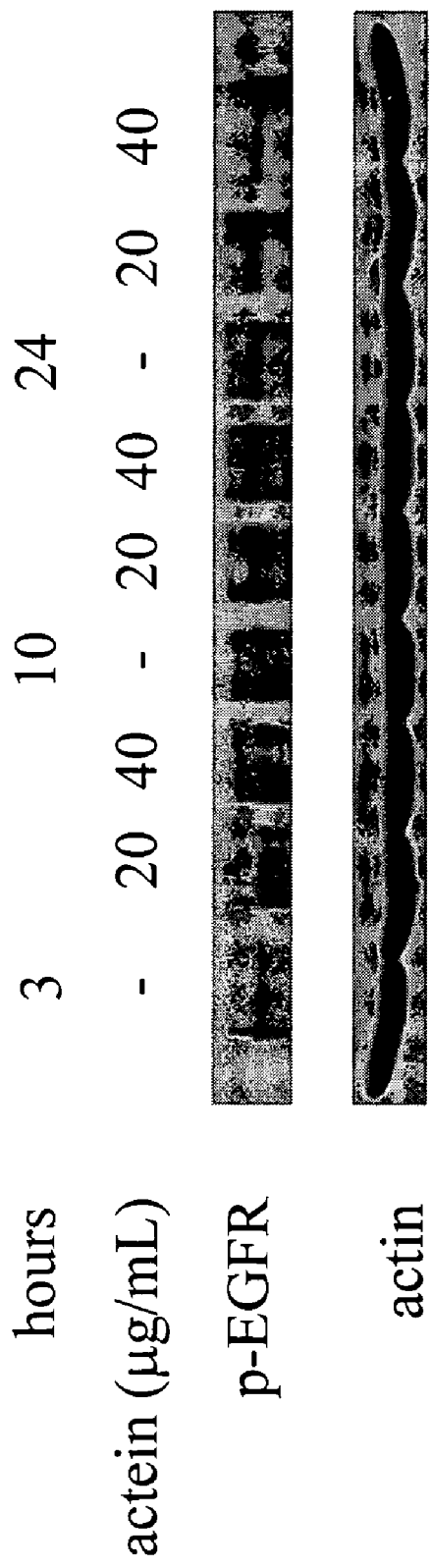

The level of the epidermal growth factor receptor (EGFR), which is overexpressed in various cancers (Masuda et al., Effects of epigallocatechin-3-gallate on growth, epidermal growth factor receptor signaling pathways, gene expression, and chemosensitivity in human head and neck squamous cell carcinoma cell lines. *Clinical Cancer Research*, 7:4220-29, 2001), was not significantly affected by treatment with actein (FIG. 6E). There was also not a consistent effect of actein on the phosphorylated and activated form of EGFR (p-EGFR). However, the inventors did observe a significant decrease with the 40 μg/ml dose at 24 h (FIG. 6F).

The Effects of Actein and the Ethyl Acetate Extract of Black Cohosh—Alone and in Combination with Chemotherapy Agents—on the Proliferation of Human Breast Cancer Cells It was essential for the inventors to explore the effects of actein (h e structure of which is set forth in FIG. 3) and extracts from black cohosh on Her2 overexpressing breast cancer cells, such as MDA-MB-453 cells, because these cells appeared to be more sensitive to inhibition by the black cohosh components, and because Her2 overexpressing breast cancers have a poorer clinical prognosis. To determine the interaction of black cohosh with chemotherapeutic drugs, actein was combined with several different classes of drugs. Among the chemotherapy drugs tested were the taxane, paclitaxel (Taxol); the selective estrogen receptor modulator (SERM), tamoxifen; the anthracycline antibiotic, doxorubicin; the anti-Her2 monoclonal antibody, herceptin (rhuMab Her2); the antimetabolite, 5-flourouracil; the platinum analog, cisplatin; and the vinca alkaloid, vinblastine. The SERM, tamoxifen, was tested on ER+MCF7 cells; the Her2 antibody and the remainder of the agents were tested on MDA-MB-453 cells. The combinations of actein with herceptin and the EtOAc extract with doxorubicin were also tested on BT474 human breast cancer cells, which form xenografts in athymic mice.

Figure 7:
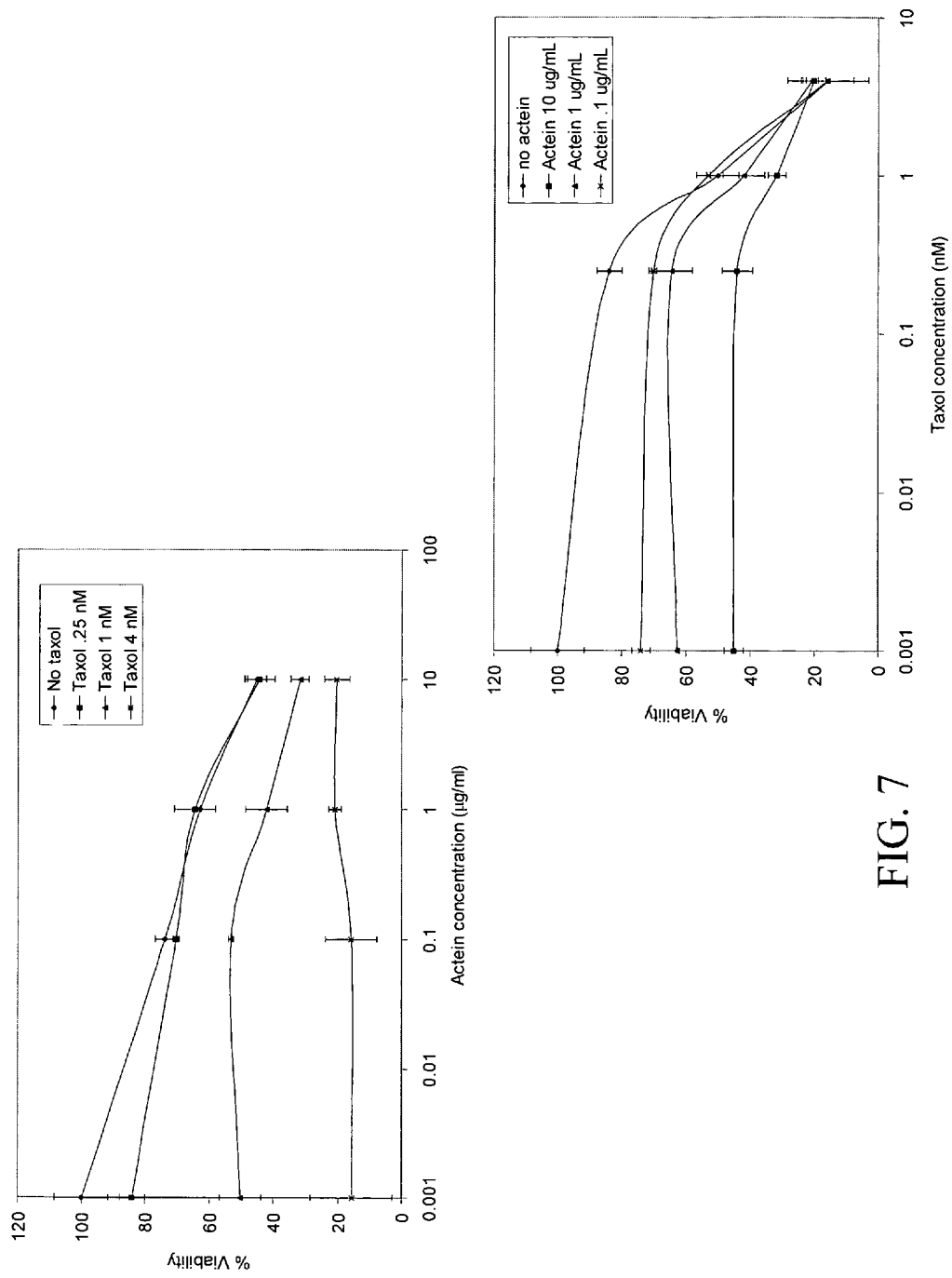
FIG. 7 shows the effects of actein alone, and in combination with paclitaxel, on cell proliferation in MDA-MB-453 (Her2 overexpressing) human breast cancer cells. MDA-MB-453 cells were treated with all combinations of 3 concentrations of actein and 3 concentrations of paclitaxel, and the solvent control, for 96 h. The number of viable cells was determined using a Coulter Counter. Similar results were obtained in two additional studies. The control contained 0.044% DMSO. bars=SD

The results for the combination of actein and Taxol are shown in FIG. 7. IC$_{50}$ values obtained from the graphs were used to calculate the combination index (CI) (Table 3). The inventors found that actein (2 μg/ml) potentiates the effect of Taxol at concentrations of 1 and 4 μM. These concentrations are reported to be attainable in the blood after treatment with Taxol.

TABLE 3

Combination index values for the combination of actein and paclitaxel on MDA-MB-453 cells.

| Taxol (nM) | Actein (μg/mL) | | | | | |
|---|---|---|---|---|---|---|
| | 0.1 | | 1 | | 10 | |
| 0.25 | 2.10 | -- | 1.70 | -- | 1.00 | +/- |
| 1 | 1.15 | -- | 0.75 | ++ | 0.05 | +++ |
| 4 | 1.10 | +/- | 0.70 | ++ | 0.00 | +++ |

Symbols:
CI
-- >1.3 antagonism
- 1.1-1.3 moderate antagonism
+/- 0.9-1.1 additive effect
+ 0.8-0.9 slight synergism
++ 0.6-0.8 moderate synergism
+++ <0.6 synergism
IC$_{50}$ values determined from the graphs in FIG. 7 were used to obtain combination index values: CI = {IC$_{50}$ (actein + paclitaxel)/IC$_{50}$ (actein alone)} + {IC$_{50}$ (paclitaxel + actein)/IC$_{50}$ (actein alone)}.

Results of Statistical Analyses

In the two-way ANOVA analysis, the F-test showed very significant differences (p values approaching to zero) among the paclitaxel concentrations, among the actein concentrations, and among the combinations of actein and paclitaxel concentrations (i.e., there were very significant interactions between the actein and paclitaxel concentrations).

The LSD t-test indicated that, under the fixed paclitaxel concentrations, 0 and 0.25 nM, there were very significant differences (p<0.01) among the four different actein concentrations. Under the paclitaxel concentration, 1 nM, there were very significant differences between the actein concentrations, 0 and 1 μg/ml, and between the actein concentrations, 0.1 and 1 μg/ml. The addition of 0.1 μg/ml actein to 1 nM paclitaxel did not produce a significant effect; however, the addition of 1 μg/ml did.

TABLE 4

2-way ANOVA.

| | 1 | 2 | 3 | average | |
|---|---|---|---|---|---|
| DMSO | 236742 | 255918 | 216444 | 236368 | 1 |
| actein .1 | 169636 | 175420 | 179339 | 174798.3 | 2 |
| actein 1 | 147900 | 148206 | 148502 | 148202.7 | 3 |
| actein 10 | 110402 | 105501 | 104339 | 106747.3 | 4 |
| tax .25 | 189954 | 205308 | 199987 | 198416.3 | 1 |
| actein .1 tax .25 | 165780 | 168440 | 164526 | 166248.7 | 2 |
| actein 1 tax .25 | 145603 | 159404 | | 152503.5 | 3 |
| actein 1 tax .25 | 107455 | 98838 | 107202 | 104498.3 | 4 |
| tax 1 | 125602 | 119850 | 110420 | 118624 | 1 |
| actein .1 tax 1 | 126449 | 125399 | | 125924 | 2 |
| actein 1 tax 1 | 105302 | 100944 | 92668 | 99638 | 3 |
| actein 10 tax 1 | 76402 | 72726 | 76398 | 75175.33 | 4 |
| tax 4 | 42388 | 35462 | 33332 | 37060.67 | 1 |
| actein .1 tax 4 | 40902 | 35448 | 35962 | 37437.33 | 2 |
| actein 1 tax 4 | 48694 | 50033 | | 49363.5 | 3 |

TABLE 4-continued

| actein 10 tax 4 | 46204 | 50002 | 48033 | 48079.67 | 4 |

Two-way ANOVA

| V.R | DF | SS | MS | F | p-value |
|---|---|---|---|---|---|
| A | 3 | 1.09E+11 | 3.64E+10 | 753.6035 | 1.35E−27 |
| B | 3 | 2.55E+10 | 8.51E+09 | 176.1761 | 1.04E−18 |
| A × B | 9 | 1.92E+10 | 2.13E+09 | 44.18546 | 1.53E−14 |
| Error | 29 | 1.4E+09 | 48318909 | | |
| Total | 44 | 1.55E+11 | | | |

Factor A is tax concentration;
Factor B is actein concentration;
A × B is combination t-test (Least Significant Difference Method; LSD)

| Combination | Average | t-value | | | p-value | | |
|---|---|---|---|---|---|---|---|
| DMSO | 236368 | | | | | | |
| actein .1 | 174798.3 | 10.8481 | | | 1.01E−11 | | |
| actein 1 | 148202.7 | 15.53406 | 4.685953 | | 1.36E−15 | 6.0678E−05 | |
| actein 10 | 106747.3 | 22.83817 | 11.99007 | 7.304113 | 4.37E−20 | 9.2448E−13 | 4.8E−08 |
| tax .25 | 198416.3 | | | | | | |
| actein .1 tax .25 | 166248.7 | 5.667697 | | | 3.98E−06 | | |
| actein 1 tax .25 | 152503.5 | 7.23546 | 2.166118 | | 5.75E−08 | 0.03866239 | |
| actein 1 tax .25 | 104498.3 | 16.54763 | 10.87994 | 7.565194 | 2.6E−16 | 9.4171E−12 | 2.44E−08 |
| tax 1 | 118624 | | | | | | |
| actein .1 tax 1 | 125924 | 1.150416 | | | 0.259371 | | |
| actein 1 tax 1 | 99638 | 3.345188 | 4.142443 | | 0.002284 | 0.00027139 | |
| actein 10 tax 1 | 75175.33 | 7.655323 | 7.997545 | 4.310135 | 1.93E−08 | 8.0625E−09 | 0.000171 |
| tax 4 | 37060.67 | | | | | | |
| actein .1 tax 4 | 37437.33 | 0.066366 | | | 0.947542 | | |
| actein 1 tax 4 | 49363.5 | 1.938819 | 1.879459 | | 0.06231 | 0.07026431 | |
| actein 10 tax 4 | 48079.67 | 1.941464 | 1.875098 | 0.202321 | 0.061975 | 0.07088192 | 0.841079 |

Bold numbers represent significant t-value and p-value.

$$t = \frac{x_1 - x_2}{\sqrt{MS(\text{error}) \times \left(\frac{1}{n_1} + \frac{1}{n_2}\right)}}$$

Similar experiments were performed on the combination of actein with herceptin, doxorubicin, cisplatin, 5-flourouracil, and vinblastine on MD-MBA-453 cells, and on the combination of actein plus tamoxifen on MCF7 cells. The same method was used to obtain the CI values for these classes of chemotherapy agents (Tables 5a and 5b).

Actein at concentrations achievable in vivo (0.2 or 2 μg/ml) potentiates the effects of several chemotherapy agents at clinically-relevant drug concentrations (Table 5a). Actein at 2 μg/ml (2.8 μM) enhances the effects of 5-FU (0.002-0.2 μg/ml; 1.54 μM), doxorubicin (0.2 μg/ml; 0.34 μM), cisplatin (2 μg/ml; 6.7 μM) and tamoxifen (2 μg/ml, 5.4 μM). Actein at 0.2 or 2 μg/ml enhances the effect of herceptin (8 μg/ml, 54 nM). At 2 μg/ml, actein has an additive effect on vinblastine (4 μg/ml).

When black cohosh was extracted with MeOH, and partitioned with EtOAc, hexane, and water, the triterpene glycosides were present primarily in the EtOAc extract. When the EtOAc extract was combined with doxorubicin or paclitaxel, synergy occurred with 2 μg/ml actein, and with 0.02-0.2 μg/ml (0.34 μM) doxorubicin or 4 nM paclitaxel (Table 5b).

TABLE 5

Combination index values for the combination of: (a) actein with various chemotherapy drugs: herceptin, tamoxifen, doxorubicin, cisplatin, 5-FU or vinblastine; and (b) EtOAc fraction with doxorubicin or paclitaxel.

(a)

| | Actein (μg/mL) | | | | | |
|---|---|---|---|---|---|---|
| 5-FU (μg/mL) | 0.2 | | 2 | | 20 | |
| 0.002 | 1.75 | -- | 0.51 | +++ | 0.23 | +++ |
| 0.02 | 1.69 | -- | 0.45 | +++ | 0.17 | +++ |
| 0.2, 0.15 uM | 1.69 | -- | 0.45 | +++ | 0.17 | +++ |

| | Actein (μg/mL) | | | | | |
|---|---|---|---|---|---|---|
| herceptin (μg/mL) | 0.2 | | 2 | | 20 | |
| 0.08 | 1.15 | − | 1.12 | − | 1.13 | − |
| 0.8 | 1.20 | − | 1.17 | − | 1.18 | − |
| 8, 54 nM | 0.35 | +++ | 0.32 | +++ | 0.33 | +++ |

| | Actein (μg/mL) | | | | | |
|---|---|---|---|---|---|---|
| tamoxifen (μg/mL) | 0.2 | | 2 | | 20 | |
| 0.5 | 1.47 | -- | 1.22 | − | 0.94 | +/− |
| 5 | 1.15 | − | 0.90 | + | 0.61 | ++ |
| 50, 134 uM | 1.07 | +/− | 0.82 | + | 0.54 | +++ |

TABLE 5-continued

Combination index values for the combination of: (a) actein with various chemotherapy drugs: herceptin, tamoxifen, doxorubicin, cisplatin, 5-FU or vinblastine; and (b) EtOAc fraction with doxorubicin or paclitaxel.

| cisplatin (µg/mL) | Actein (µg/mL) | | | | | |
|---|---|---|---|---|---|---|
|  | 0.2 | | 2 | | 20 | |
| 0.2 | 3.33 | -- | 1.93 | -- | 1.44 | -- |
| 2 | 2.11 | -- | 0.71 | ++ | 0.22 | +++ |
| 20, 67 uM | 2.04 | -- | 0.64 | ++ | 0.15 | +++ |

| vinblastine (µg/mL) | Actein (µg/mL) | | | | | |
|---|---|---|---|---|---|---|
|  | 0.2 | | 2 | | 20 | |
| 0.4 | 4.40 | -- | 4.45 | -- | 4.08 | -- |
| 4 | 0.95 | +/- | 1.00 | +/- | 0.63 | ++ |
| 40, 44 uM | 0.95 | +/- | 1.00 | +/- | 0.63 | ++ |

(b)

| doxorubicin (µg/mL) | EtOAc (µg/mL) | | | | | |
|---|---|---|---|---|---|---|
|  | 0.2 | | 2 | | 20 | |
| 0.002 | 1.13 | - | 1.21 | - | 0.75 | ++ |
| 0.02 | 0.43 | +++ | 0.51 | +++ | 0.05 | +++ |
| 0.2, 0.34 uM | 0.43 | +++ | 0.50 | +++ | 0.04 | +++ |

| taxol (nM) | EtOAc (µg/mL) | | | | | |
|---|---|---|---|---|---|---|
|  | 0.2 | | 2 | | 20 | |
| 0.25 | 1.89 | -- | 1.86 | -- | 1.86 | -- |
| 1 | 1.08 | +/- | 1.05 | +/- | 1.05 | +/- |
| 4 | 0.79 | ++ | 0.76 | ++ | 0.76 | ++ |

Symbols:
CI
-- >1.3 antagonism
- 1.1-1.3 moderate antagonism
+/- 0.9-1.1 additive effect
+ 0.8-0.9 slight synergism
++ 0.6-0.8 moderate synergism
+++ <0.6 synergism
$IC_{50}$ values were determined from the combination of 3 concentrations of actein and 3 concentrations of the specific chemotherapy agent and the solvent control, as illustrated for the combination of actein and paclitaxel in Table 3.

TABLE 6

Combination index values for the combination of actein with the EtOAc fraction and cimigenol with paclitaxel.

| actein (µg/ml) | EtOAc (µg/ml) | | | | | |
|---|---|---|---|---|---|---|
|  | EtOAc .2 | | EtOAc 2 | | EtOAc 20 | |
| actein .2 | 3.8166 | -- | 3.8166 | -- | 3.96666 | -- |
| actein 2 | 3.65 | -- | 3.65 | -- | 3.8 | -- |
| actein 20 | 0.15126 | +++ | 0.15126 | +++ | 0.30126 | +++ |

| Taxol (µg/ml) | Cimigenol (µg/ml) | | | | | |
|---|---|---|---|---|---|---|
|  | cimi .2 | | cimi 2 | | cimi 20 | |
| tax .25 | 1.5023 | -- | 1.5023 | -- | 1.4665 | -- |
| tax 1 | 1.85714 | -- | 1.85714 | -- | 1.82142 | -- |
| tax 4 | 0.85714 | + | 0.85714 | + | 0.82142 | + |

TABLE 7

Combination index values for the combination of actein with herceptin and the EtOAc fraction of black cohosh with doxorubicin on BT474 human breast cancer cells.

| herceptin (µg/mL) | Actein (µg/mL) | | | | | |
|---|---|---|---|---|---|---|
|  | 0.2 | | 2 | | 20 | |
| 0.8, 5.4 nM | 3.14 | -- | 3.06 | -- | 3.06 | -- |
| 8 | 0.08 | +++ | 0 | +++ | 0 | +++ |
| 32 | 0.08 | +++ | 0 | +++ | 0 | +++ |

| doxorubicin (µg/mL) | EtOAc (µg/mL) | | | | | |
|---|---|---|---|---|---|---|
|  | 0.2 | | 2 | | 20 | |
| 0.002 | 1.45 | -- | 1.79 | -- | 0.79 | ++ |
| 0.02 | 0.67 | ++ | 1 | +/- | 0 | +++ |
| 0.2, 0.34 uM | 0.67 | ++ | 1 | +/- | 0 | +++ |

Symbols:
CI
-- >1.3 antagonism
- 1.1-1.3 moderate antagonism
+/- 0.9-1.1 additive effect
+ 0.8-0.9 slight synergism
++ 0.6-0.8 moderate synergism
+++ <0.6 synergism
$IC_{50}$ values were determined from the combination of 3 concentrations of actein and 3 concentrations of the specific chemotherapy agent and the solvent control.

To further understand the effect of actein and the EtOAc fraction of black cohosh, the investigators tested the effects on BT474 human breast cancer cells ($ER^+$, her2 overexpressing, 25-fold), which can form tumors in athymic mice. The investigators obtained strong synergy when actein (0.2 or 2 µg/ml) was combined with herceptin (0.8 or 8 µg/ml) and additive effects when the EtOAc fraction (2 µg/ml) was combined with doxorubicin (0.02 µg/ml, 34 nM).

Actein, or the fraction enriched for triterpene glycosides, could be used in combination with agents, in single use (including paclitaxel, herceptin, and tamoxifen), to treat breast cancer. If actein or the triterpene glycoside fraction is free of significant side effects, they could be used in combination with herceptin for long-term treatment of patients with metastatic disease.

Effects of Actein, in Combination with Chemotherapy Agents on the Distribution of Cells in the Cell Cycle To understand the nature of the interaction of actein with the different classes of chemotherapy agents, we determined the effect of actein in combination with various chemotherapy agents on the distribution of cells in the cell cycle. When the cells were synchronized by serum starvation followed by serum stimulation, treatment with actein induced a dose dependent increase in the percent of cells in G1 at 48 hours (Table 8a). When actein (2 or 20 µg/ml) was combined with paclitaxel (1 nM), or when actein (20 µg/ml) was combined with doxorubicin (0.1 µg/ml, nM) or 5 FU (0.02 µg/ml, nM), there was a synergistic increase in the percent of cells in the $subG_1$ phase at 48 hours, an indicator of apoptosis (Table 8b, c).

In the case of doxorubicin and 5 FU, the addition of actein to the chemotherapy agent resulted in an increase in cells in the G1 phase of the cell cycle (Table 8). The inventors' results indicate that it may be better to give the chemotherapy agents before actein, in order to retain the block at S or G2/M that is induced by some chemotherapy agents.

TABLE 8

Effect of actein alone and in combination with chemotherapy agents on cell cycle distribution in MDA-MB-453 cells.

|  | Sub G1 (%) | G1 (%) | S (%) | G2/M (%) |
|---|---|---|---|---|
| Table 8a |||||
| (a) The cells were grown in DMEM + 0.25% FBS for 48 hrs and then treated with actein at 20 µg/ml or 40 µg/ml and analyzed at 48 hrs by DNA flow cytometry. The values indicate the % of cells in the indicated phases of the cell cycle. The control contains 0.08% DMSO. |||||
| dmso, 0.08% | 2.1 | 74.3 | 10.5 | 13.6 |
| actein, 20 µg/ml | 1.8 | 79.6 | 8.5 | 10.0 |
| actein, 40 µg/ml | 2.2 | 83.8 | 4.9 | 9.0 |
| Table 8b |||||
| (b) The cells were treated with 0, 2 or 20 µg/ml (29.6 µM) actein alone and in combination with paclitaxel (1 nM) and analyzed at 48 hrs by DNA flow cytometry. The values indicate the % of cells in the indicated phases of the cell cycle. The control contains 0.044% DMSO. |||||
| Dmso | 1.0 | 70.6 | 11.8 | 17.0 |
| Actein 2 µg/mL | 0.9 | 69.8 | 11.0 | 18.6 |
| Actein 20 µg/mL | 1.6 | 70.8 | 9.7 | 18.2 |
| Taxol 1 nM | 1.0 | 71.0 | 10.8 | 17.0 |
| Taxol 1 nM + Actein 2 µg/mL | 1.8 | 69.2 | 10.6 | 18.5 |
| Taxol 1 nM + Actein 20 µg/mL | 2.8 | 70.1 | 8.6 | 18.9 |
| Table 8c |||||
| c. The cells were treated with 0 or 20 µg/ml (29.6 µM) actein alone and in combination with doxorubicin (0.1 µg/ml, 0.17 µM), 5-FU (0.02 µg/ml, 0.15 µM) and analyzed at 48 hrs by DNA flow cytometry. The values indicate the % of cells in the indicated phases of the cell cycle. The control contains 0.08% DMSO. |||||
| dmso, 0.08% | 3.0 | 59.0 | 10.0 | 28.0 |
| Actein, 20 µg/mL | 2.7 | 59.2 | 8.6 | 29.5 |
| Doxorubicin, 0.1 µg/mL | 2.5 | 30.1 | 5.6 | 61.7 |
| Doxorubicin + Actein, 20 µg/mL | 5.3 | 39.2 | 9.6 | 46.0 |
| 5- FU, 0.02 µg/mL | 3. | 28.9 | 47.6 | 20.3 |
| 5- FU + Actein, 20 µg/mL | 6.8 | 38.0 | 34.1 | 21.2 |

Effects of Actein on Proteins Involved in Carcinogenesis

The inventors' previous results indicated that actein decreased the level of cyclin D1, cdk4, and the hyperphosphorylated form of the pRB protein, and increased the level of p21$^{cip1}$ in MCF7 cells—changes that may contribute to the arrest in G1. The level of the epidermal growth factor receptor (EGFR), which is overexpressed in various cancers (Suzui et al., Growth inhibition of human hepatoma cells by acyclic retinoid is associated with induction of p21 (CIP1) and inhibition of expression of cyclin D1. *Cancer Research*, 62:3997-4006, 2002), was not altered after treatment with actein. There also was no consistent effect of actein on the phosphorylated and activated form of EGFR (p-EGFR). However, the inventors did see a significant decrease of p-EGFR with the 40 µg/ml dose at 24 h. Thus, the EGFR did not appear to be a direct target for actein.

Figure 8:
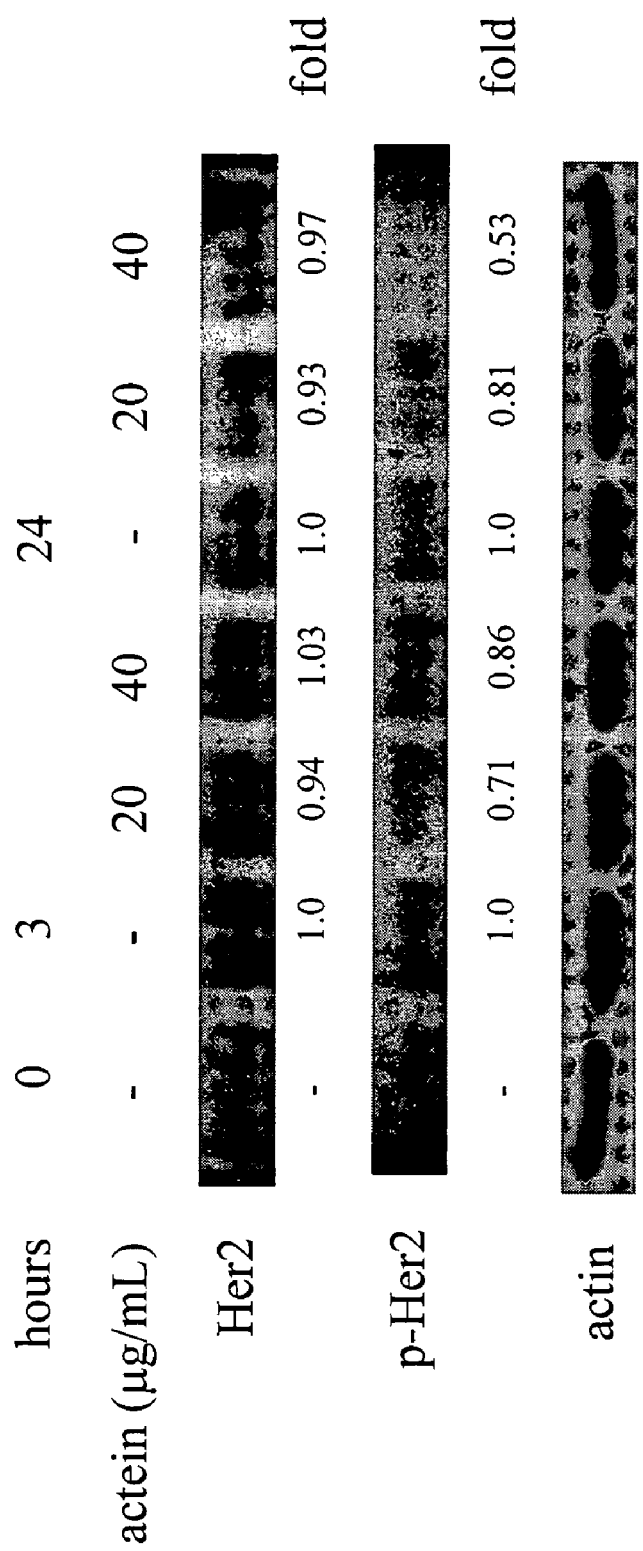
FIG. 8 illustrates a Western-blot analysis of extracts obtained from MDA-MB-453 cells treated with actein. The cells were treated with 0, 20, or 40 µg/ml of actein. After 3 and 24 h, extracts were prepared and analyzed by Western blotting with an antibody to Her2 or an antibody to phospho-Her2 (p-Her2). An antibody to β-actin was used as a loading control. The staining intensities of the visualized blots were quantified using NIH image software. For each protein, the relative band intensities were determined by comparing treated samples with untreated controls. These values were then normalized (fold), using β-actin as an internal control.

Since the Her2 overexpressing cells were the most sensitive to growth inhibition by black cohosh extracts and components, the inventors tested the effect of actein on the Her2 receptor and on the phosphorylation and activation of the Her2 receptor (p-Her2) (FIG. 8) in MDA-MB-453 human breast cancer cells (which express both Her2 and p-Her2 at high levels). Actein at 20 µg/ml caused a slight decrease in the level of the Her2 protein at 3 and 24 h. After exposure to actein at 20 or 40 µg/ml, there was a small effect on p-Her2 at 3 h. The inventors found that actein at 20 or 40 µg/ml induced a dose-dependent decrease in the level of the p-Her2 receptor at 24 h. It is not clear how actein inhibits phosphorylation. For example, it is not clear whether actein binds to and directly inhibits the kinase activity of the Her2 receptor, analogous to the action of Iressa (Masuda et al., Epigallocatechin-3-gallate inhibits activation of HER-2/neu and downstream signaling pathways in human head and neck and breast carcinoma cells. *Clin. Cancer Res.*, 9: 3486-91, 2003), or whether it inhibits activation of the other component of the heterodimeric complex.

Figure 18:
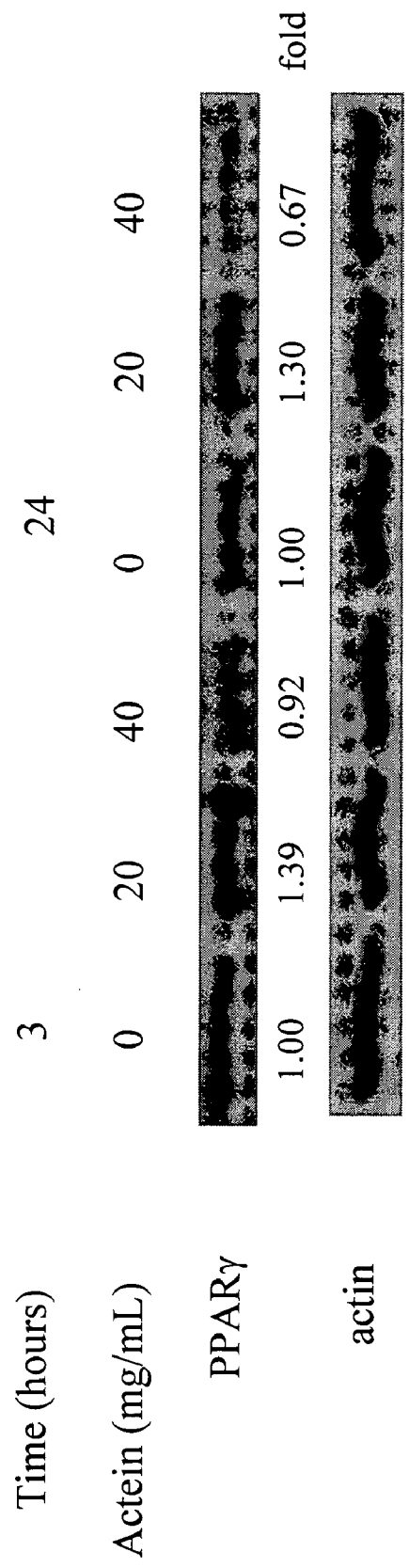
FIG. 18 illustrates MDA-MB-453 cells that were treated with 0, 20, or 40 µg/ml actein (20 µg/ml actein is equivalent to 29.6 µM). After 3 and 24 h, extracts were analyzed by Western blotting, with an antibody to PPARγ. An antibody for β-actin was used as a loading control.

As the synthetic triterpenoid 2-cyano-3,12-dioxooleana-1, 9-dien-28-oic acid (CDDO) is a ligand for PPAR-γ (Wang et al., 2000; Lapillonne et al, 2003), the inventors next tested the effect of actein on PPAR-γ (FIG. 18). After treatment with actein, the intensities of the PPAR-γ bands relative to the β-actin bands were: 1.39 (3 h, 20 µg/ml), 0.93(3 h, 40 µg/ml), 1.3 (24 h, 20 µg/ml), and 0.67 (24 h, 40 µg/ml). Thus actein 20 µg/ml increased the level of PPARγ at 3 and 24 hours. This anti-inflammatory protein is therefore among the targets of actein.

Effects of Actein on Transcriptional Control of Specific Genes

To further determine the nature of the target of actein, the inventors tested the effect of actein on molecules, such as cyclin D1, that function downstream of active Her2-containing heterodimers. Since the inventors found that actein induces cell-cycle arrest at G1, it was of interest to examine the effects of this compound on cellular levels of proteins that control cell-cycle progression. Cyclin D1 was of particular interest, because it plays a critical role in mediating the transition from G1 to S, is overexpressed in about 50-60% of primary human breast carcinomas (Joe et al., Resveratrol induces growth inhibition, S-phase arrest, apoptosis, and changes in biomarker expression in several human cancer cell lines. *Clin. Cancer Res.*, 8:893-903, 2002), and is overexpressed in several human breast cancer cell lines (Soh et al., Novel roles of specific isoforms of protein kinase C in activation of the c-fos serum response element. *Mol. Cel. Bio.*, 19:1313-24, 1999).

Figure 9:
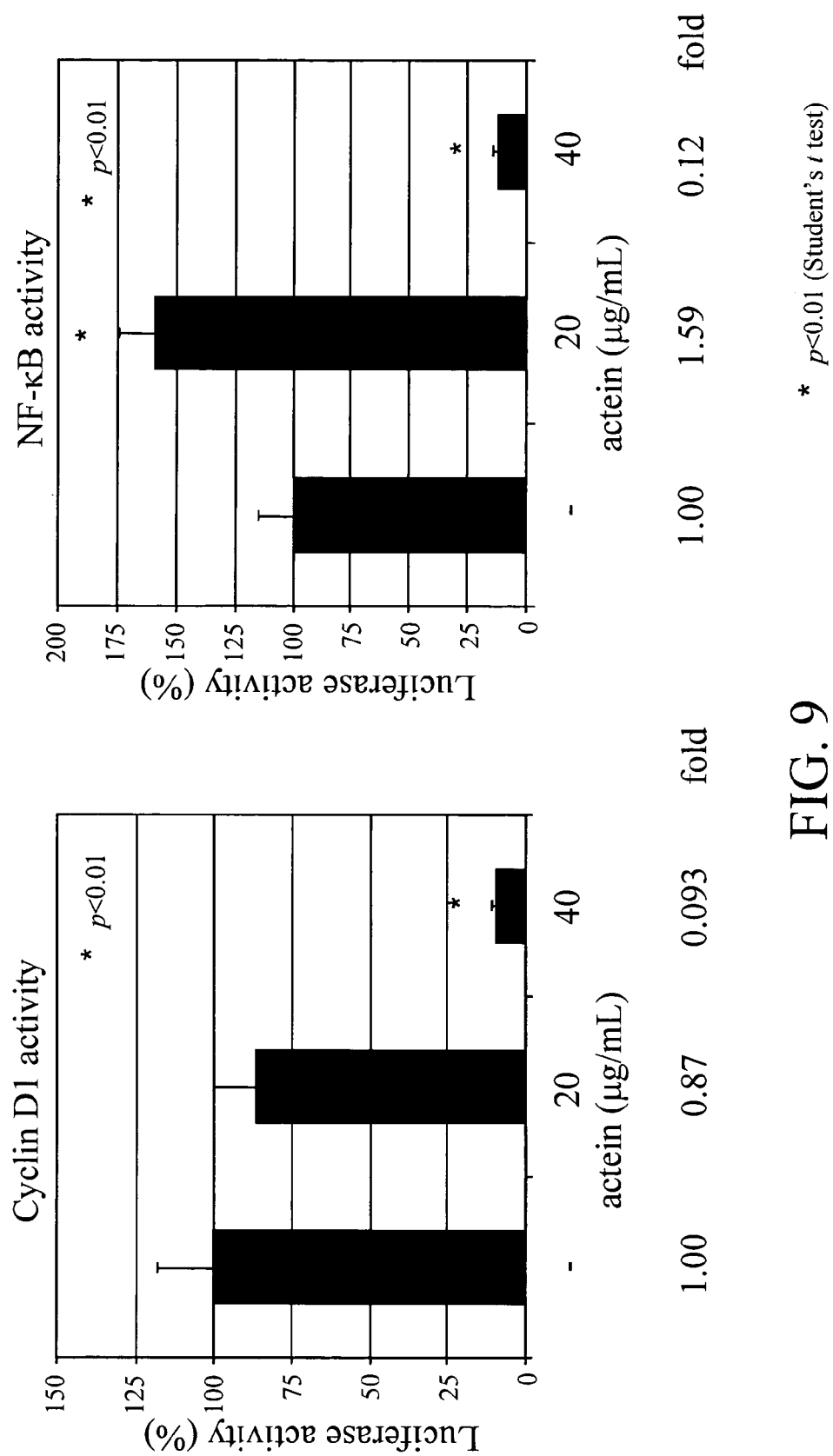
FIG. 9 presents a reporter promoter analysis of extracts obtained from MDA-MB-453 cells treated with actein. Using lipofectin, triplicate samples of MDA-MB-453 breast cancer cells were co-transfected with DNA of the indicated reporter plasmid, using β-gal DNA as an internal control. The cells were then treated with actein at 0, 20, and 40 µg/ml, in quadruplicate. Luciferase and β-gal activities were determined, as previously described (Masuda et al., Effects of epigallocatechin-3-gallate on growth, epidermal growth factor receptor signaling pathways, gene expression, and chemosensitivity in human head and neck squamous cell carcinoma cell lines. *Clinical Cancer Research*, 7:4220-29, 2001). Luciferase activities were normalized to β-gal activities. left panel=cyclin D1; right panel=nuclear factor kappa B (NF-κB); bars=SD FIG. 10 sets forth the effects of the aglycone cimigenol and the triterpene glycosides cimigenol glycoside, and actein, purified from black cohosh, on cell proliferation in MDA-MB-453 cells. MDA-MB-453 cells were exposed to increasing concentrations of the indicated purified components for 96 h, and the number of viable cells was determined using a Coulter Counter.
Figure 10:
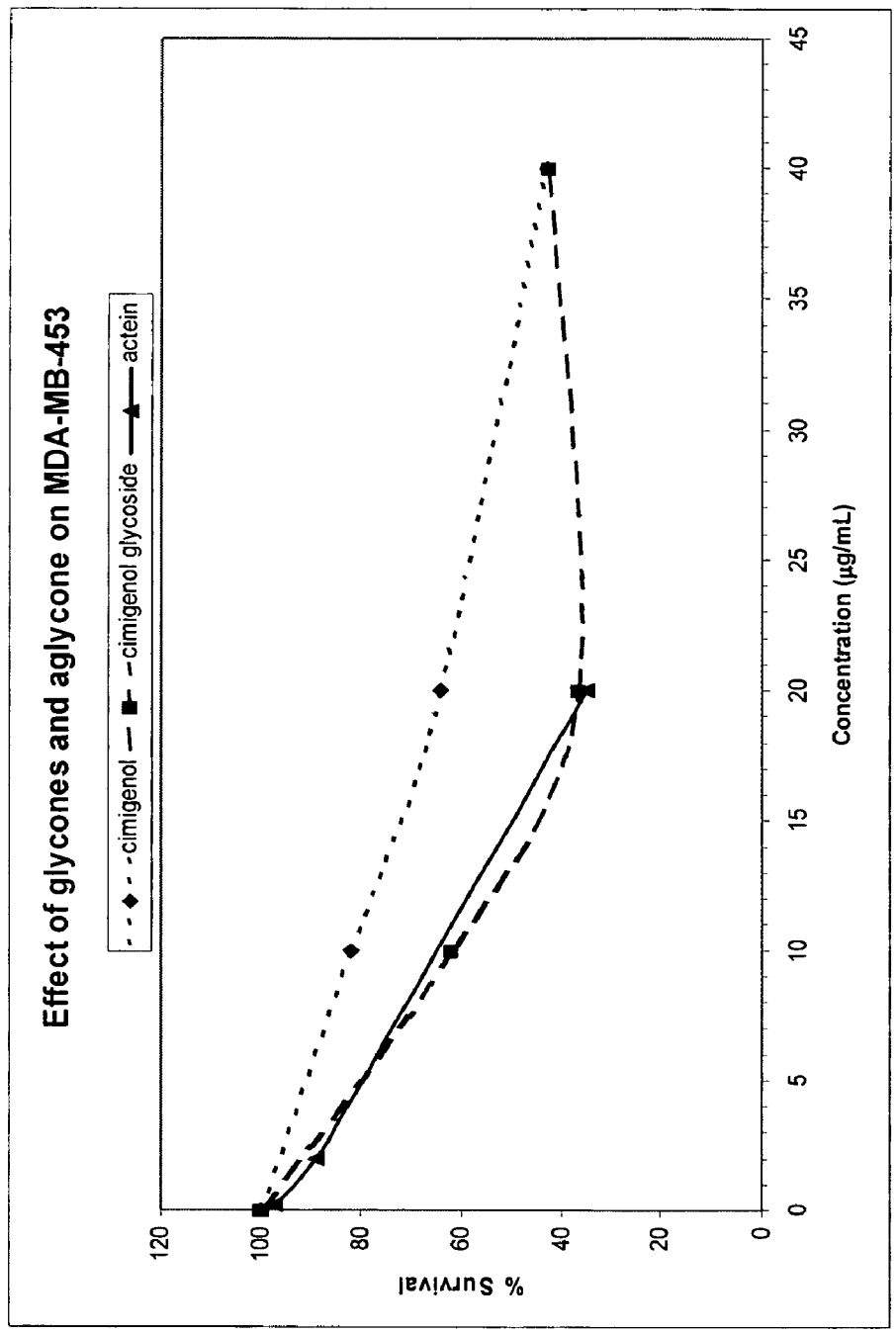
Figure 13:
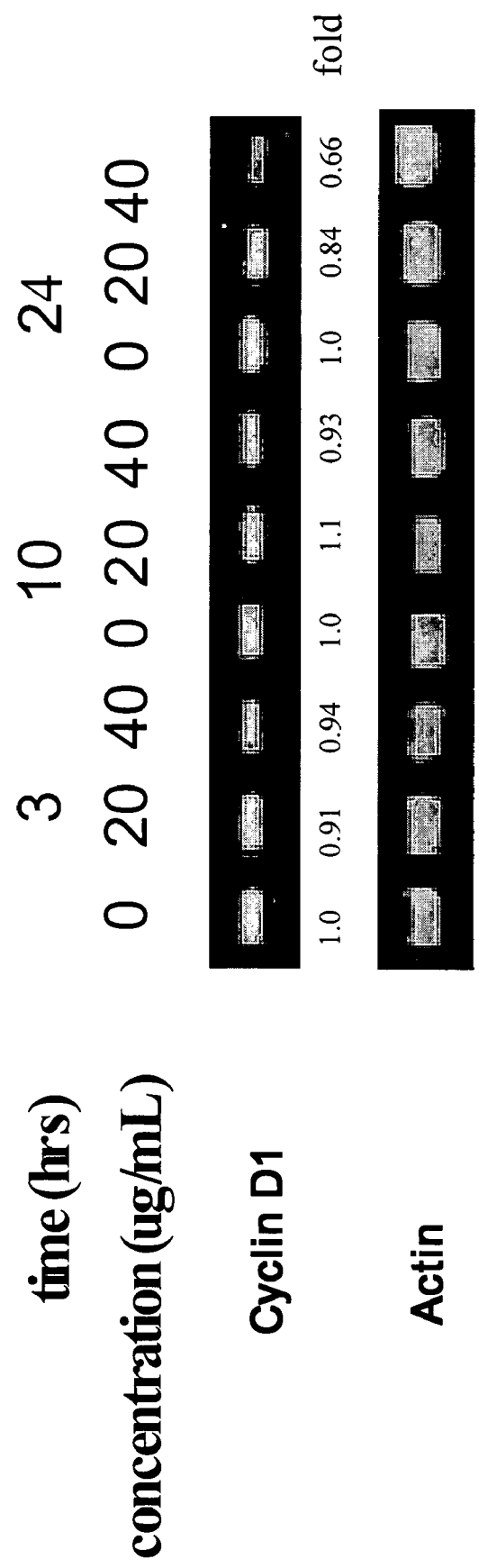
FIG. 13 illustrates the effects of actein on cyclin D1 mRNA in MCF7 cells (RT-PCR). MCF7 cells were treated with DMSO or actein for 3, 10, or 24 h. RNA was isolated and analyzed by RT-PCR, using primers for cyclin D1 and actin (control). The staining intensities of the visualized blots were quantified using NIH image software. The relative band intensities were determined by comparing treated samples with untreated controls. These values were then normalized (fold), using β-actin as an internal control.
Figure 14:
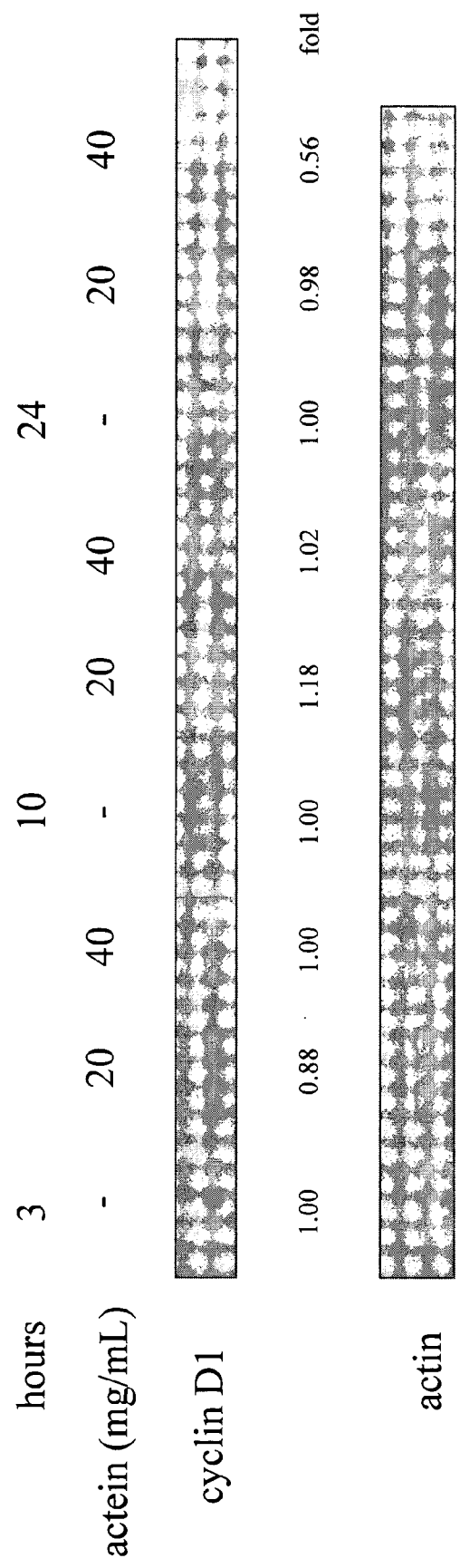
FIG. 14 demonstrates the effects of actein on cyclin D1 mRNA in MDA-MB-453 cells (RT-PCR). MDA-MB-453 cells were treated with DMSO or actein for 3, 10, or 24 h. RNA was isolated and analyzed by RT-PCR, using primers for cyclin D1 and actin (control). The staining intensities of the visualized blots were quantified using NIH image software. The relative band intensities were determined by comparing treated samples with untreated controls. These values were then normalized (fold), using β-actin as an internal control.
Figure 15:
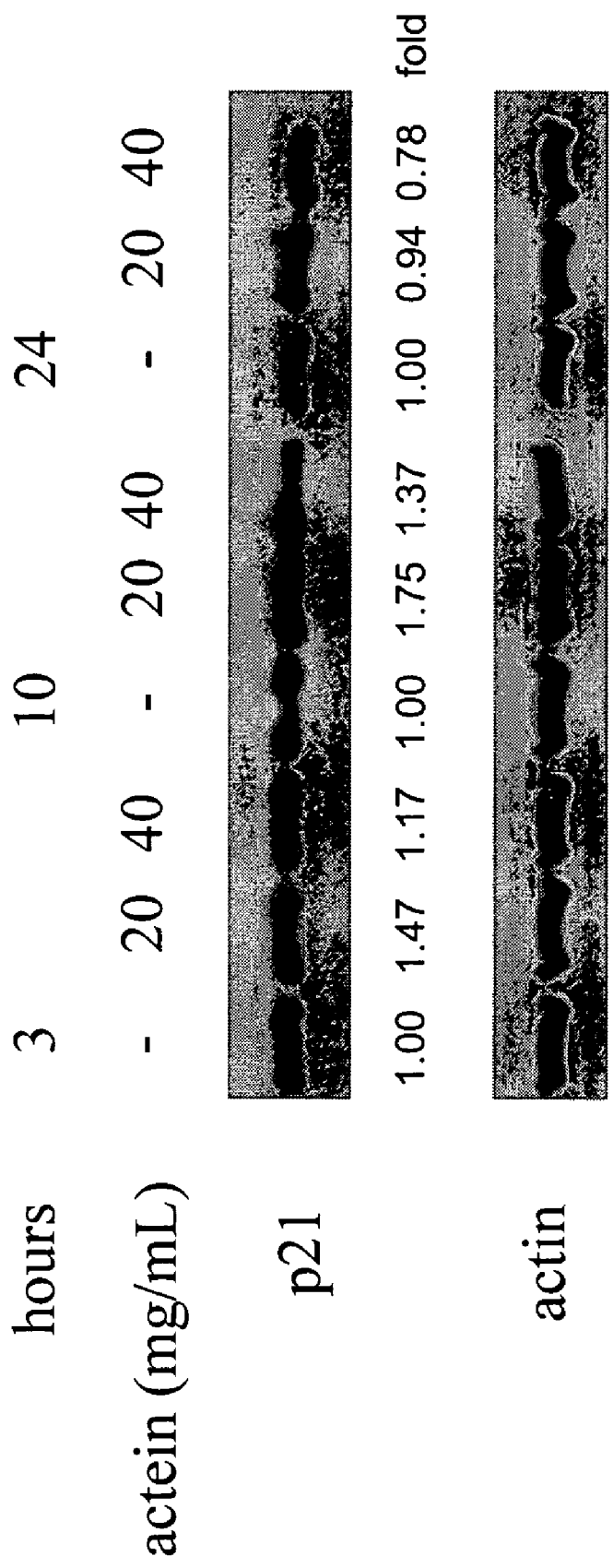
FIG. 15 illustrates MCF7 cells treated with 0, 20, or 40 µg/ml actein. 20 µg/ml actein is equivalent to 29.6 µM. After 3, 10, and 24 h, extracts were analyzed by Western blotting with an antibody to p21. An antibody for β-actin was used as a loading control.
Figure 16:
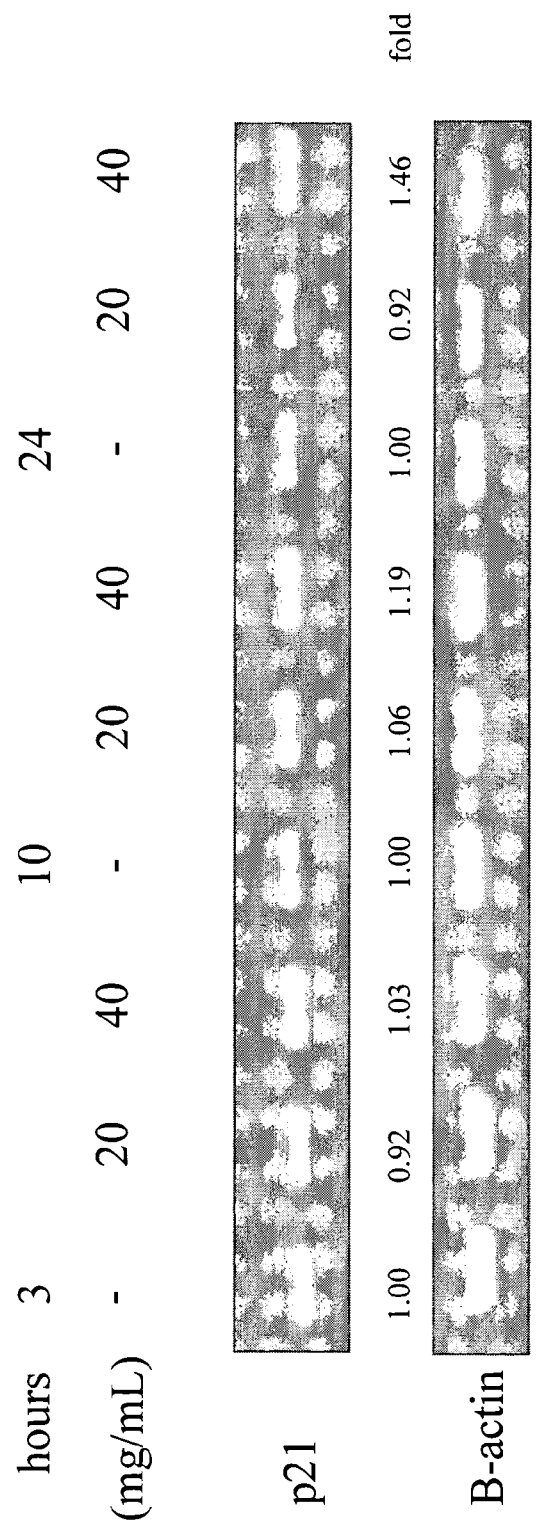
FIG. 16 shows the effects of actein on p21 mRNA in MDA-MB-453 cells (RT-PCR). MDA-MB-453 cells were treated with DMSO or actein for 3, 10, or 24 h. RNA was isolated and analyzed by RT-PCR, using primers for cyclin D1 and actin (control). The staining intensities of the visualized blots were quantified using NIH image software. The relative band intensities were determined by comparing treated samples with untreated controls. These values were then normalized (fold), using β-actin as an internal control.

Actein suppressed the level of cyclin D1 protein in MDA-MB-453 cells. After treatment with actein, the intensities of the cyclin D1 bands relative to the β-actin bands were: 3 hr, 40 µg/ml: 0.93; 24 hr, 20 µg/ml: 1.3; 40 µg/ml: 0.44. The inventors further show that actein at 40 µg/ml reduced the level of cyclin D1 mRNA at 24 hours, 0.66-fold in MCF7 cells (FIG. 13) and 0.56-fold in MDA-MB-453 cells (FIG. 14). The inventors next examined the effect of actein on cyclin D1 transcriptional promoter activity in MDA-MB-453 cells, using transient transfection reporter assays (Soh et al., Novel roles of specific isoforms of protein kinase C in activation of the c-fos serum response element. *Mol. Cell. Biol.*, 19:1313-24, 1999; Soh et al., Cyclic GMP mediates apoptosis induced by sulindac derivatives via activation of c-Jun NH2-terminal kinase 1. *Clin. Cancer Res.*, 10:4136-41, 2000; Masuda et al., Effects of epigallocatechin-3-gallate on growth, epidermal growth factor receptor signaling pathways, gene expression, and chemosensitivity in human head and neck squamous cell carcinoma cell lines. *Clin. Cancer Res.*, 7:4220-29, 2001). To accomplish this, the inventors used luciferase promoter sequences that were 1745 bp upstream of the cyclin D1 gene. At 24 hours after exposure to actein at 20 (0.87 fold) or 40 µg/ml (0.093 fold), there was a dose dependent decrease in promoter activity, compared to β-gal as a control (FIG. 9). This result, in addition to the inventors' Western-blot data, suggests that actein inhibits the expression of cyclin D1 at the level of transcription.

Figure 17:
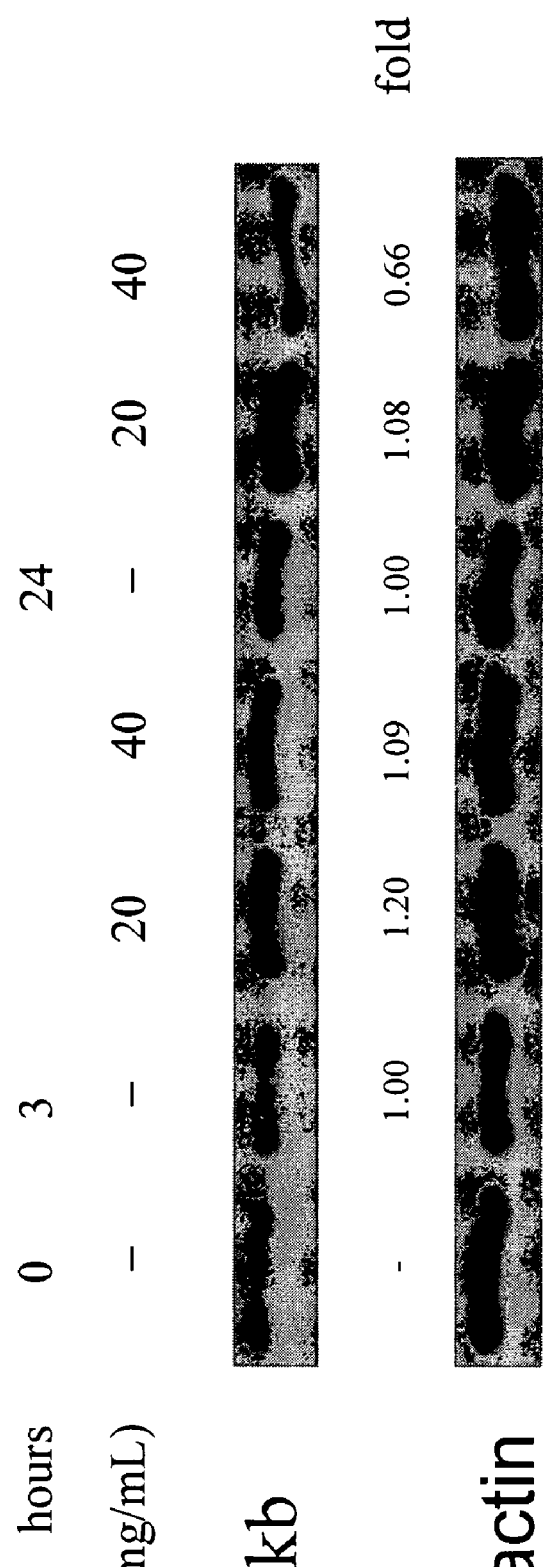
FIG. 17 illustrates MDA-MB-453 cells that were treated with 0, 20, or 40 µg/ml actein. 20 µg/ml actein is equivalent to 29.6 µM. After 3, 10, and 24 h, extracts were analyzed by Western blotting, with an antibody to ikβ. An antibody for β-actin was used as a loading control.

Since NF-kB is instrumental in controlling cell proliferation, the inventors then explored the effect of actein on NF-kB promoter activity. Actein at 20 µg/ml induced an increase (1.59 fold) and, at 40 µg/ml, a decrease (0.12 fold), in NF-kB promoter activity (FIG. 9). To understand the basis for this effect, the inventors checked the effect of actein on the level of the related proteins, IκB and IκκB. After treatment with actein, the intensities of the IκB bands relative to the β-actin bands were: 1.2 (3 h, 20 µg/ml), 1.09 (3 h, 40 µg/ml), 0.81 (24 h, 20 µg/ml), and 0.53 (24 h, 40 µg/ml) (FIG. 17). After treatment with actein, the intensities of the IκκB bands relative to the β-actin bands were: 1.79 (3 h, 20 µg/ml), 1.78 (3 h, 40 µg/ml), 0.48 (10 h, 20 µg/ml), 0.59 (10 h, 40 µg/ml), 1.06 (24 h, 20 µg/ml, and 0.95 (24 h, 40 µg/ml).

In summary, the EtOAc fraction of black cohosh: (1) inhibits cell proliferation at ~20 and 10 µg/ml, in ER+ and ER− human breast cancer cell lines, respectively; and (2) induces cell-cycle arrest at G1 at low concentrations (~$IC_{50}$), and at G2/M at high concentrations (~3×$IC_{50}$).

The triterpene glycoside fraction of black cohosh, and the triterpene glycosides—actein, 23-epi-26-deoxyactein, cimifugoside, and cimiracemoside A—inhibit the growth of human breast cancer cells, and induce cell cycle arrest at G1.

In MCF7 cells, actein decreases the level of cyclin D1, cdk4, and ppRb and increases the level of p21 and p27—changes which lead to G1 arrest. It reduces the level of cyclin D1 mRNA and promoter activity, thereby acting at the level of transcription. Actein does not affect the level of EGFR, and, therefore, does not specifically act through the estrogen receptor, the Her2 receptor, or the EGFR receptor. Actein is capable of enhancing the effects of tamoxifen on MCF7 breast cancer cells.

In MDA-MB-453 cells, actein decreases the level of p-Her2 and the level of cyclin D1 mRNA and promoter activity at 24 h. It increases the level of p21 mRNA at 24 h. Its effects on the level of NF-κB promoter activity is complex: actein increase the level of NF-κB promoter activity at 20 µg/ml while decreases the level at 40 µg/ml at 24 h. Actein is capable of enhancing the effects of paclitaxel, herceptin, 5-FU, doxorubicin, and cisplatin.

While the foregoing invention has been described in some detail for purposes of clarity and understanding, it will be appreciated by one skilled in the art, from a reading of the disclosure, that various changes in form and detail can be made without departing from the true scope of the invention in the appended claims.

TABLE 9

Summary.

| molecule | assay | 0 | 3 hr, - | 20 ug/ml | 40 ug/ml | 10 hr, - | 20 ug/ml | 40 ug/ml | 24 hr, - | 20 ug/ml | 40 ug/ml |
|---|---|---|---|---|---|---|---|---|---|---|---|
| cyclin D1 | promoter | MDA-MB-453 | | | | | | | 1 | 0.87 | 0.093 |
| CD1 RNA | RT-PCR | MDA-MB-453 | 1 | 0.88 | 1 | 1 | 1.18 | 1.02 | 1 | 0.98 | 0.56 |
| CD1 RNA | RT-PCR | MCF7 | 1 | 0.91 | 0.94 | 1 | 1.1 | 0.93 | 1 | 0.84 | 0.66 |
| cyclin D1 | | MDA-MB-453 | 1 | | 0.93 | | | | 1 | 1.3 | 0.44 |
| p-Her2 | WB | MDA-MB-453 | 1 | 0.71 | 0.86 | | | | 1 | 0.81 | 0.53 |
| p21 | WB | MCF7 | 1 | 1.47 | 1 | 1 | 1.75 | 1.37 | 1 | 0.94 | 0.78 |
| | RT-PCR | MDA-MB-453 | 1 | 0.92 | 1.03 | 1 | 1.06 | 1.19 | 1 | 0.92 | 1.46 |
| ppRB | WB | MCF7 | 1 | 1.51 | 1.59 | 1 | 0.61 | 0.64 | 1 | 0.8 | 0.43 |
| PPAR-g | | | 1 | 1.39 | 0.92 | | | | 1 | 1.3 | 0.67 |
| NF-kB | promoter | MDA-MB-453 | | | | | | | 1 | 1.59 | 0.12 |
| ikb | WB | MDA-MB-453 | 1 | 1.2 | 1.09 | | | | 1 | 0.81 | 0.53 |
| ikkb | WB | MDA-MB-453 | 1 | 1.79 | 1.78 | 1 | 0.48 | 0.59 | 1 | 1.06 | 0.95 |

What is claimed is:

1. A composition for use in treating neoplasia, comprising an effective anti-neoplastic amount of an ethyl acetate fraction of a methanol/water extract of roots and rhizomes of *Actaea racemosa L.*

2. The composition of claim 1, wherein the ethyl acetate fraction comprises at least one triterpene glycoside compound.

3. The composition of claim 2, wherein the triterpene glycoside compound is selected from the group consisting of actein, cimifugoside, cimigenol glycoside, cimiracemoside A, and 23-epi-26-deoxyactein.

4. The composition of claim 3, wherein the triterpene glycoside compound is actein.

5. The composition of claim 4, wherein the effective anti-neoplastic amount of actein is between about 0.5 µg/ml and about 40.0 µg/ml.

6. The composition of claim 5, wherein the effective anti-neoplastic amount of actein is between about 1.0 µg/ml and about 3.0 µg/ml.

7. The composition of claim 1, wherein the ethyl acetate fraction comprises at least one aglycone.

8. The composition of claim 7, wherein the at least one aglycone is cimigenol.

9. A composition comprising from about 20 µg/ml to about 40.0 µg/ml of an ethyl acetate fraction of a methanol/water extract of roots and rhizomes of *Actaea racemosa L.*, which comprises at least one triterpene glycoside compound.

* * * * *